US009115187B2

(12) United States Patent
Smith et al.

(10) Patent No.: US 9,115,187 B2
(45) Date of Patent: Aug. 25, 2015

(54) IDENTIFICATION OF ANTIBODIES SPECIFIC FOR LYSSAVIRUSES AND METHODS OF THEIR USE

(75) Inventors: Todd G. Smith, Decatur, GA (US); Xianfu Wu, Atlanta, GA (US)

(73) Assignee: **The United States of America as

FIG. 1

ERA backbone

ERA with G333 mutation

ERA with two introduced transcriptional (trans) units

Insert MOKV and WCBV G genes

ERA with three glycoprotein genes (ERA-3G)

IDENTIFICATION OF ANTIBODIES SPECIFIC FOR LYSSAVIRUSES AND METHODS OF THEIR USE

CROSS REFERENCE TO RELATED APPLICATION(S)

This is the U.S. National Stage of International Application No. PCT/US2011/056738, filed Oct. 18, 2011, published in English under PCT Article 21(2), which claims the benefit of U.S. Provisional Application No. 61/394,651, filed Oct. 19, 2010, which is incorporated by reference herein in its entirety.

FIELD

This disclosure concerns methods of identifying lyssavirus-specific antibodies and the use of such antibodies in the treatment and prophylaxis of rabies.

BACKGROUND

Rabies is an inevitably fatal but preventable disease. In developing countries rabies remains a significant endemic disease burden. World-wide approximately 55,000 people die of rabies each year (WHO Expert Consultation on Rabies, 2004). Rabies is preventable with proper early post-exposure treatment. Currently, post-exposure prophylaxis includes thorough wound-washing with soap and water followed by administration of vaccine and anti-rabies virus immunoglobulin (RIG) of human or equine origin. RIG administered shortly after exposure at the wound site provides passive immunity which neutralizes rabies virus and prevents its spread until the patient's immune response following vaccination is elicited. Deaths due to post-exposure prophylaxis failure are most commonly attributed to deviations from the recommended regimen such as late initiation of post-exposure prophylaxis or no administration of RIG (Wilde, *Vaccine*, 25:7605-7609, 2007). In developing countries, availability of RIG is extremely low with only 1-2% of post-exposure prophylaxis being performed using RIG (Sudarshan et al., *Int J Infect Dis*, 11:29-35, 2007; WHO Consultation on a Monoclonal Antibody Cocktail for Rabies Post Exposure Treatment, 2002). In the United States, only human derived RIG is administered due to the risk of anaphylactic shock from exposure to equine immunoglobulins, but the concern of blood-born pathogen transmission in human RIG remains.

Human monoclonal antibodies (mAbs) that neutralize rabies virus have long been recognized as an alternative to overcome the limitations of RIG (Dietzschold et al., *J Virol*, 64:3087-3090, 1990). Adequate supplies of cell-cultured human mAbs could be produced in a cost-effective manner (Prosniak et al., *J Infect Dis*, 188:53-56, 2003). In addition, the use of human mAbs reduces the likelihood of an adverse immune response (Weiner, *J Immunother*, 29:1-9, 2006) and has been shown to be as effective as RIG in preventing rabies in animals (de Kruif et al., *Annu Rev Med*, 58:359-368, 2007). When a cocktail of two rabies-neutralizing, human mAbs was given with a rabies vaccine to animals experimentally infected with rabies, dose-dependent survival was observed, and all animals receiving the highest dose survived (Goudsmit et al., *J Infect Dis*, 193:796-801, 2006). The same cocktail was recently shown to be safe to administer to healthy humans in two phase-one clinical trials (Bakker et al., *Vaccine*, 26:5922-5927, 2008). However, selection of human monoclonal antibodies to include in such a cocktail has some limitations. The diversity of mAbs produced depends significantly on the diversity of viral antigens used to immunize human donors.

Rabies virus is a member (genotype 1) of the genus Lyssavirus. This genus also includes rabies-like viruses (genotypes 2-7) which can cause rabies disease in humans (Bourhy et al., *Virology*, 194:70-81, 1993; Gould et al., *Virus Res*, 54:165-187 1998). These viruses have a non-segmented, negative-sense, single-stranded RNA genome that encodes five proteins (Sokol et al., *Virology*, 38:651-665, 1969; Sokol et al., *J Virol*, 7:241-249, 1971). In the mature virion, RNA-dependent RNA polymerase, phosphoprotein, and nucleocapsid protein are associated with the genomic RNA while matrix protein and glycoprotein (G protein) surround it (Wiktor et al., *J Immunol*, 110:269-276, 1973). Trimeric G protein "spikes" coat the surface of the virion and as the only surface exposed protein, is responsible for attachment and entry into host cells. This also makes G protein the primary antigen for induction of virus-neutralizing antibodies, and G protein-specific mAbs are included in the cocktails currently being developed for post-exposure prophylaxis (Dietzschold et al., *J Virol*, 64:3087-3090, 1990; Kramer et al., *Eur J Immunol*, 35:2131-2145, 2005; Wunner et al., "Rabies Virus" in Rabies (Second Edition)," pp. 23-68, Academic Press, Oxford, 2007).

SUMMARY

Disclosed herein is a method of identifying an antibody (or antigen-binding fragment thereof) that specifically binds a plurality of lyssaviruses. Antibodies identified by the methods provided herein can be used, for example, for post-exposure rabies prophylaxis or in the treatment of clinical rabies.

Provided herein is a method of identifying a monoclonal antibody or antigen-binding fragment thereof that specifically binds at least two different lyssaviruses. In some embodiments, the method includes screening a naïve antibody phage display library with at least two different lyssavirus glycoproteins, such as by panning the library against a recombinant virus expressing at least two different lyssavirus glycoproteins, panning the library against recombinant glycoprotein from at least two different lyssaviruses, panning the library against at least two different cell lines expressing different lyssavirus glycoproteins, or any combination thereof.

In particular embodiments, the method includes screening a naïve antibody phage display library with (1) a recombinant rabies virus expressing glycoprotein from rabies virus (RABV), Mokola virus (MOKV) and West Caucasian bat virus (WCBV); (2) recombinant glycoprotein from at least two of RABV, MOKV, WCBV, Lagos bat virus (LBV) and Duvenhage virus (DUVV); and/or (3) at least two different cell lines expressing different lyssavirus glycoproteins selected from RABV, MOKV, WCBV, LBV and DUVV glycoprotein. The method further includes selecting a phage display clone that specifically binds to at least two different lyssaviruses, at least two different lyssavirus glycoproteins, or both.

In some embodiments, the phage display library is a naïve human $V_H$ domain library.

Also provided are isolated monoclonal antibodies (or antigen-binding fragments thereof) identified according to the methods disclosed herein and their use in the treatment or prophylaxis of rabies.

Further provided are isolated monoclonal antibodies (or antigen-binding fragments thereof) that specifically bind at least two different lyssaviruses or that specifically bind recombinant glycoprotein from at least two different lyssaviruses. In some embodiments, the $V_H$ domain of the antibody is encoded by a nucleotide sequence at least 85% identical to any one of SEQ ID NOs: 1-110. Also provided are methods of treating rabies in a subject by administering to the subject a monoclonal antibody disclosed herein.

Expression vectors, such as an Fc IgG expression vector, comprising the nucleotide sequence of any one of SEQ ID NOs: 1-110 are also provided by the present disclosure. In some embodiments, the expression vector further comprises the nucleotide sequence of a variable light ($V_L$) domain from a lyssavirus-specific (such as rabies virus-specific) monoclonal antibody. A cell comprising an expression vector disclosed herein is further provided. Also provided are monoclonal antibodies encoded by the expression vectors. A method of treating rabies in a subject by administering to the subject a monoclonal antibody expressed by an expressed vector disclosed herein is also provided.

The foregoing and other objects, features, and advantages of the invention will become more apparent from the following detailed description, which proceeds with reference to the accompanying figures.

BRIEF DESCRIPTION OF THE FIGURES

FIG. 1: Construction of ERA-3G. The G333 mutation is introduced into the ERA backbone and two transcriptional (trans) units are added. The transcriptional units are introduced between the P and M genes and between the G and L genes. The MOKV and WCBV G genes are cloned into the transcriptional units to form a recombinant ERA rabies virus with three glycoprotein genes (ERA-3G).

SEQUENCES

Figure 2:
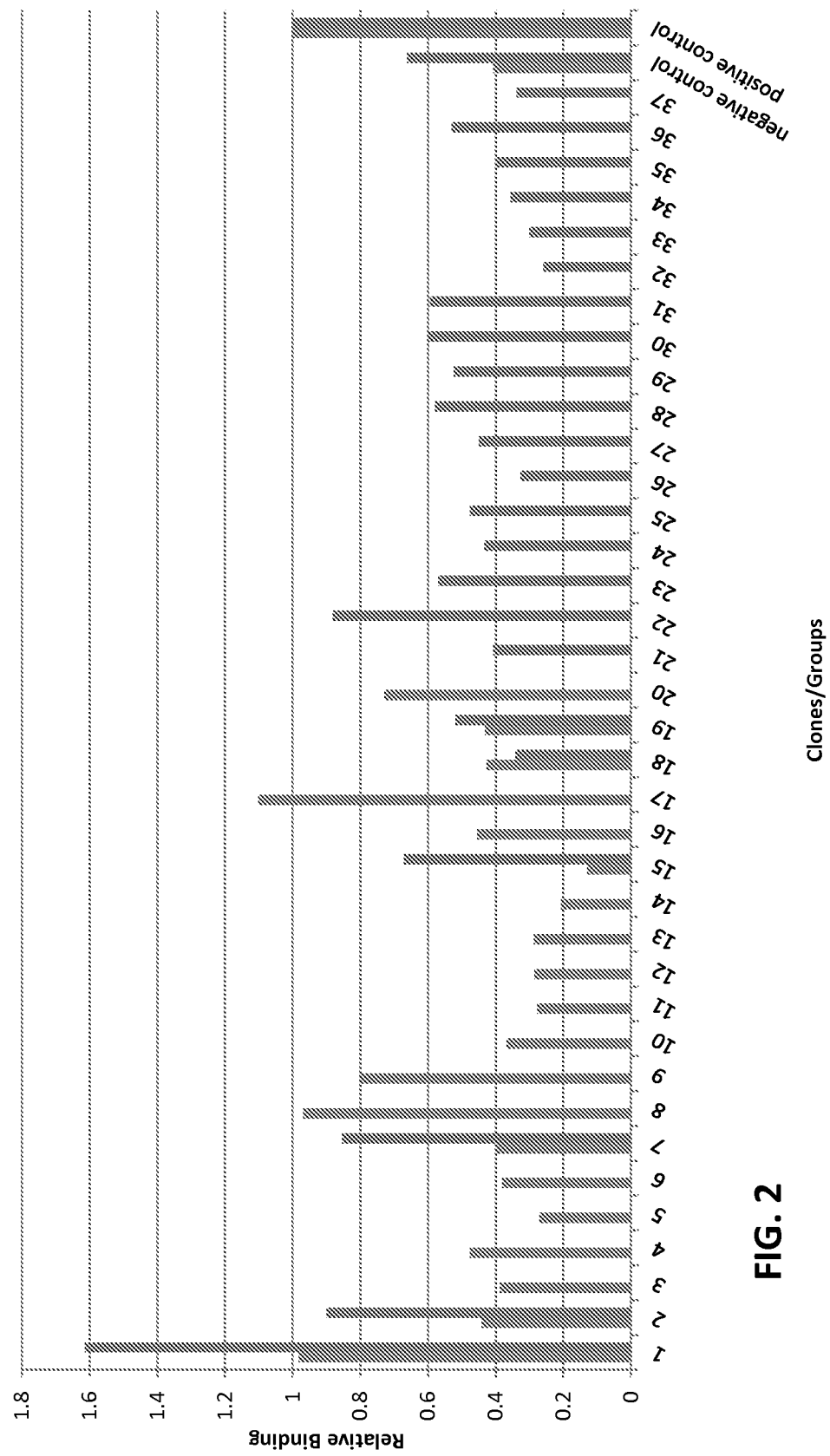
FIG. 2: Results of whole virus ELISA. Relative binding of selected human variable heavy ($V_H$) domain phage display clones to recombinant ERA RABV expressing glycoprotein (G) from RABV, MOKV and WCBV. The left bar for each clone shown indicates clones selected using the whole recombinant virus ERA RABV expressing glycoprotein (G) from RABV, MOKV and WCBV. The right bar for each clone shown indicates clones selected using glycoproteins purified from the recombinant ERA RABV expressing glycoprotein (G) from RABV, MOKV and WCBV. Using a standard ELISA method, raw absorbance (420 nm-650 nm) was fixed relative to a known clone binding to its cognate antigen (positive control).

The nucleic acid and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 8, 2013, 102 KB, which is incorporated by reference herein. In the accompanying sequence listing:

SEQ ID NOs: 1-43 are the nucleotide sequences of human variable heavy ($V_H$) domain phage display clones selected using a recombinant ERA RABV expressing glycoprotein (G) from RABV, MOKV and WCBV.

SEQ ID NOs: 44-110 are the nucleotide sequences of human variable heavy ($V_H$) domain phage display clones identified by sequential selection on cells expressing LBV glycoprotein, cells expressing MOKV glycoprotein, cells expressing WCBV glycoprotein and cells expressing DUVV glycoprotein.

SEQ ID NOs: 111 and 112 are the nucleotide sequences of RT-PCR primers for amplification of the MOKV G gene.

SEQ ID NOs: 113 and 114 are the nucleotide sequences of RT-PCR primers for amplification of the WCBV G gene.

SEQ ID NO: 115 is the nucleotide sequence of MOKV G.

SEQ ID NO: 116 is the nucleotide sequence of WCBV G.

SEQ ID NO: 117 is the nucleotide sequence of a transcription unit for incorporating heterologous ORFs.

SEQ ID NO: 118 is the nucleotide sequence of LBV G.

SEQ ID NO: 119 is the nucleotide sequence of DUVV G.

DETAILED DESCRIPTION

I. Abbreviations

ABLV Australian bat lyssavirus
ARAV Aravan virus
BBLV Bokeloh bat lyssavirus
CDR complementarity determining region
dAb domain antibody
DUVV Duvenhage virus
EBLV-1 European bat lyssavirus-1
EBLV-2 European bat lyssavirus-2
ELISA enzyme-linked immunosorbent assay
ERA Evelyn-Rokitnicki-Abelseth
G glycoprotein
IRKV Irkut virus
KHUV Khujand virus
L RNA-dependent RNA polymerase
LBV Lagos bat virus
M matrix protein
mAb monoclonal antibody
MOKV Mokola virus
N nucleoprotein
P phosphoprotein
RABV rabies virus
RIG anti-rabies virus immunoglobulin
RNP ribonucleoprotein
RABV rabies virus
RFFIT rapid fluorescent focus inhibition test
SHIBV Shimoni bat virus
$V_H$ variable heavy
$V_L$ variable light
WCBV West Caucasian bat virus II. Terms and Methods Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of*

*Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administer:

As used herein, administering a composition, such as an antibody, to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal:

Living multi-cellular vertebrate organisms, a category that includes, for example, mammals and birds. The term mammal includes both human and non-human mammals. The term "animal" includes both human and veterinary subjects, for example, humans, non-human primates, dogs, cats, horses, raccoons, bats, rats, mice, foxes, squirrels, opossum, coyotes, wolves and cows.

Antibody:

A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Each heavy and light chain contains a constant region and a variable region (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., *Sequences of Proteins of Immunological Interest*, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds a specific antigen will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies. As used herein "monoclonal antibodies" further includes antigen-binding fragments, such as Fv, scFv, dsFv or Fab fragments.

A "chimeric antibody" has framework residues from one species, such as human, and CDRs (which generally confer antigen binding) from another species, such as a murine antibody.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. All parts of a human immunoglobulin are substantially identical to corresponding parts of natural human immunoglobulin sequences.

Antibody Binding Affinity:

The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope. Binding affinity can be measured using any technique known in the art, such as end-point titration in an Ag-ELISA assay.

Antigen:

A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Complementarity Determining Region (CDR):

Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively.

Effector Molecule (EM):

The portion of a chimeric molecule that is intended to have a desired effect on a cell or system or substance to which the chimeric molecule is targeted. The term effector molecule is interchangeable with effector moiety, therapeutic agent, diagnostic agent, and similar terms.

Therapeutic agents include such compounds as nucleic acids, proteins (including monoclonal antibodies and antigen-binding fragments of monoclonal antibodies), peptides, amino acids or derivatives, glycoproteins, radioisotopes, lipids, carbohydrates, recombinant viruses or toxins. Nucleic acid therapeutic and diagnostic moieties include antisense nucleic acids, derivatized oligonucleotides for covalent cross-linking with single or duplex DNA, and triplex forming oligonucleotides. Diagnostic agents or moieties include radioisotopes and other detectable labels. Detectable labels useful for such purposes are also well known in the art, and include radioactive isotopes such as $^{32}P$, $^{125}I$ and $^{131}I$, fluorophores, chemiluminescent agents, and enzymes.

Evelyn-Rokitnicki-Abelseth (ERA):

The ERA strain of rabies virus was derived from the Street-Alabama-Dufferin (SAD) strain, first isolated from a rabid dog in Alabama (USA) in 1935. The ERA strain was derived after multiple passages of SAD rabies virus in mouse brains, baby hamster kidney (BHK) cells, and chicken embryos.

Framework Region:

Amino acid sequences interposed between CDRs (or hypervariable regions). Framework regions include variable light and variable heavy framework regions. Each variable domain comprises four framework regions, often referred to as FR1, FR2, FR3 and FR4. The framework regions serve to hold the CDRs in an appropriate orientation for antigen binding. Framework regions typically form β-sheet structures.

Fusion Partner:

Refers to any molecule that is fused (such as covalently linked) to another molecule. In the context of the present disclosure, an immunoconjugate includes an antibody linked to a fusion partner. In some examples, the fusion partner is an effector molecule, a label (such as a detectable label), a heterologous polypeptide or a drug.

Fusion Protein:

A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons in that frame.

Immunoconjugate:

A covalent linkage of a fusion partner, such as an effector molecule, label, heterologous polypeptide or other moiety, to an antibody or antigen binding fragment thereof. The linkage can be by chemical or recombinant means, for instance. In some cases, the linkage is chemical, wherein a reaction between the antibody moiety and the fusion partner has produced a covalent bond formed between the two molecules to form one molecule. A peptide linker (short peptide sequence) can optionally be included between the antibody and the effector molecule.

Inhibiting or Treating a Disease:

Inhibiting the full development of a disease or condition, for example, in a subject who is at risk for a disease. One specific example of a disease is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated:

An "isolated" or "purified" biological component (such as a nucleic acid, peptide, protein, protein complex, antibody or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label:

A detectable compound or composition that is conjugated directly or indirectly to another molecule to facilitate detection of that molecule. Specific, non-limiting examples of labels include fluorescent tags, enzymatic linkages, and radioactive isotopes.

Lyssavirus:

A genus of viruses that is part of the Rhabdoviridae family within the order Mononegavirales (viruses with a single-stranded, negative sense genome). Lyssaviruses are the etiological agents of rabies encephalitis in warm-blooded animals and humans. Lyssavirus species include rabies virus (RABV; genotype 1), Lagos bat virus (LBV; genotype 2), Mokola virus (MOKV; genotype 3), Duvenhage virus (DUVV; genotype 4), European bat lyssavirus-1 (EBLV-1; genotype 5), European bat lyssavirus-2 (EBLV-2; genotype 6) Australian bat lyssavirus (ABLV; genotype 7) and six additional species isolated from bats: four in central Asia and Russia (Aravan virus—ARAV; Khujand virus—KHUV; Irkut virus—IRKV; and West Caucasian bat virus—WCBV), one in Africa (Shimoni bat virus—SHIBV) and one in Europe (Bokeloh bat lyssavirus—BBLV) (Kuzmin et al., *Emerg. Infect. Dis.* 14(12):1887-1889, 2008; Weyer et al., *Epidemiol. Infect.* 136:670-678, 2007; Kuzmin et al., *Virus Res.* 149(2): 197-210, 2010; Freuling et al., *Emerg. Infect. Dis.* 17(8): 1519-22, 2011; Kuzmin and Rupprecht, "Bat rabies" In *Rabies*, 2$^{nd}$ Edition, New York, Academic Press, 2007, pages 259-307, Jackson and Wunner, eds.).

Neutralizing Antibody:

An antibody that is capable of protecting a subject (or cells) against infection.

ORF (Open Reading Frame):

A series of nucleotide triplets (codons) coding for amino acids without any termination codons. These sequences are usually translatable into a peptide.

Operably Linked:

A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Phage Display:

A method for the study of protein-protein, protein-peptide, and protein-DNA interactions that uses bacteriophages to connect proteins with the genetic information that encodes them. Antibody phage display libraries, and methods of generating such libraries, are well known in the art (see, for example, Famm et al., *J. Mol. Biol.* 376:926-931, 2008; Car-men and Jermutus, *Brief Funct Genomic Proteomic* 1(2):189-203, 2002; and U.S. Pat. Nos. 6,828,422 and 7,195,866). In the context of the present disclosure, an antibody phage display library is a library of any type of antigen-binding antibody fragment displayed on phage. In particular examples, the antibody phage display library is a $V_H$ domain phage display library, or a scFv phage display library. As used herein, a "naïve" antibody (or antibody domain) phage display library refers to a library constructed using subjects that have not been exposed to lyssavirus.

Pharmaceutically Acceptable Carriers:

The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, proteins or antibodies that bind these proteins, viruses or vectors, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide:

A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced. Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |

-continued

| Original Residue | Conservative Substitutions |
| --- | --- |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Purified:

The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Rabies:

A viral disease that causes acute encephalitis (inflammation of the brain) in warm-blooded animals. Rabies is zoonotic (transmitted by animals), most commonly by a bite from an infected animal but occasionally by other forms of contact. Rabies is almost frequently fatal if post-exposure prophylaxis is not administered prior to the onset of severe symptoms. Rabies is caused by viruses of the Lyssavirus genus.

Rabies Virus (RABV or RV):

A member of the Rhabdoviridae family having a non-segmented RNA genome with negative sense polarity. Rabies virus is the prototype of the Lyssavirus genus. The rabies virus Evelyn-Rokitnicki-Abelseth (ERA) strain is a strain derived from the Street-Alabama-Dufferin (SAD) strain, first isolated from a rabid dog in Alabama (USA) in 1935. The ERA strain was derived after multiple passages of SAD RABV in mouse brains, baby hamster kidney (BHK) cells, and chicken embryos. The complete genomic sequence of the ERA strain is disclosed in PCT Publication No. WO 2007/047459.

Recombinant:

A recombinant nucleic acid, protein or virus is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. In some embodiments, recombinant rabies virus is generated using reverse genetics, such as the reverse genetics system described in PCT Publication No. WO 2007/047459. In some examples, the recombinant rabies viruses comprise one or more mutations in a viral virulence factors, such as glycoprotein. In other examples, the recombinant rabies viruses comprise a heterologous gene, such as a sequence encoding a glycoprotein from another lyssavirus (such as Mokola virus, West Caucasian bat virus or Lagos bat virus).

Sequence Identity:

The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject:

Living multi-cellular vertebrate organisms, a category that includes both human and non-human mammals.

Therapeutically Effective Amount:

A quantity of a specified agent sufficient to achieve a desired effect in a subject being treated with that agent. For example, this may be the amount of a lyssavirus-specific monoclonal antibody useful for treating rabies. The effective amount of a lyssavirus-specific monoclonal antibody useful for treating rabies in a subject will be dependent on, for example, the subject being treated, the manner of administration of the composition, and other factors.

Vector:

A nucleic acid molecule that can be introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art. In some embodiments herein, the vector is an Fc IgG expression vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Currently available anti-rabies immunoglobulins do not neutralize lyssaviruses of other genotypes, such as Lagos bat virus (LBV), Mokola virus (MOKV), and West Caucasian bat virus (WCBV). The use of immunized humans for immune library construction biases libraries towards neutralization of genotype 1 rabies viruses with lower cross-reactivity towards other genotypes. To circumvent this limitation, disclosed herein is the use of a naïve human phage display library to identify and characterize novel monoclonal antibodies (mAbs) that broadly neutralize lyssaviruses. As described in Examples 2 and 3 below, this library displays variable heavy ($V_H$) domain antibodies (dAbs) with diversity added to the complement determining regions (CDR). Antibodies identified by the methods provided herein can be used, for example, for post-exposure rabies prophylaxis or in the treatment of clinical rabies.

Provided herein is a method of identifying a monoclonal antibody or antigen-binding fragment thereof that specifically binds at least two different lyssaviruses. In some embodiments, the method includes screening a naïve antibody phage display library with at least two different lyssavirus glycoproteins, such as by screening the library against a recombinant virus expressing at least two different lyssavirus glycoproteins, screening the library against recombinant glycoprotein from at least two different lyssaviruses, screening the library against cells expressing at least two different lyssavirus glycoproteins, or any combination thereof. In some embodiments, the method further includes selecting a phage display clone that specifically binds to at least two different lyssaviruses, at least two different lyssavirus glycoproteins, or both.

The at least two different lyssaviruses can be selected from any known lyssavirus, such as, for example, rabies virus (RABV), Mokola virus (MOKV), West Caucasian bat virus (WCBV), Lagos bat virus (LBV), Duvenhage virus (DUVV), European bat lyssavirus-1 (EBLV-1), European bat lyssavirus-2 (EBLV-2), Australian bat lyssavirus (ABLV), Aravan virus (ARAV), Khujand virus (KHUV) and Irkut virus (IRKV). In some embodiments, the antibody or antigen-binding fragment specifically binds at least three, at least four or at least five different lyssaviruses, or at least three, at least four or at least five different lyssavirus glycoproteins.

In particular embodiments, the method includes screening a naïve antibody phage display library with (1) a recombinant rabies virus expressing glycoprotein from RABV, MOKV and WCBV; (2) at least two different recombinant lyssavirus glycoproteins selected from the RABV glycoprotein, the MOKV glycoprotein, the WCBV glycoprotein, the LBV glycoprotein and the DUVV glycoprotein; or (3) at least two different cell lines expressing a lyssavirus glycoprotein selected from the RABV glycoprotein, the MOKV glycoprotein, the WCBV glycoprotein, the LBV glycoprotein and the DUVV glycoprotein; and selecting a phage display clone that specifically binds to at least two different lyssaviruses, at least two different lyssavirus glycoproteins, or both. In some examples, the at least two different lyssaviruses are selected from RABV, MOKV, WCBV, LBV and DUVV. In particular non-limiting examples, the antibody or antigen-binding fragment specifically binds whole virus and/or glycoprotein of RABV, MOKV and WCBV; RABV, MOKV, WCBV and LBV; RABV, MOKV, WCBV, LBV and DUVV; or MOKV, WCBV, LBV and DUVV.

In some embodiments, the phage display library is a naïve human $V_H$ domain library. In other embodiments, the phage display library is a naïve human scFv library or a naïve human Fab library. However, other naïve human antibody libraries can be used and an appropriate library can be selected by one of skill in the art.

In some embodiments, the antigen-binding fragment comprises a $V_H$ domain. In other embodiments, the antigen-binding fragment comprises a scFV. In yet other embodiments, the antigen-binding fragment comprises an Fab.

In some embodiments, the method further includes cloning the antigen-binding fragment (for example, a fragment comprising a $V_H$ domain, a scFV or a Fab) into an Fc IgG expression vector to generate an immunoglobulin molecule containing the fragment (such as an Fc IgG1 expression vector, for example pNUT-Cγ1 (Boel, et al., *J. Immunol. Methods.* 239: 153-166, 2000)). In some examples, the Fc IgG expression vector further includes nucleic acid sequence encoding a variable light ($V_L$) domain from a rabies virus-specific antibody.

Selecting a phage display clone that specifically binds to a lyssavirus (for example, whole virus) or lyssavirus glycoprotein can be performed using any assay known in the art for evaluating antigen binding. In some embodiments, the selecting step includes an ELISA to detect specific binding to lyssavirus glycoprotein, whole virus, or both.

In some embodiments, the method further includes screening the phage display clone for lyssavirus neutralization. Assays for evaluating virus neutralization are well known in the art and include, for example, fluorescent focus assays, including the rapid fluorescent focus inhibition test (RFFIT).

Also provided are isolated monoclonal antibodies, and antigen-binding fragments thereof, identified according to the methods disclosed herein. In some embodiments, the antibody neutralizes infectivity of the lyssaviruses.

In some embodiments, the $V_H$ domain of the antibody is encoded by a nucleotide sequence at least 85%, at least 90%, at least 95%, at least 96%, at least 97%, at least 98% or at least 99% identical to any one of SEQ ID NOs: 1-110. In some examples, the $V_H$ domain of the antibody is encoded by a nucleotide sequence comprising any one of SEQ ID NOs: 1-110.

In some embodiments, any in-frame "TAG" (stop codons) in the $V_H$ domain sequence are changed to "GAG" (glutamate codons) to allow expression in eukaryotic cells.

SEQ ID NOs: 1-43 show the nucleotide sequences of 43 different clones of a naïve human $V_H$ domain library that were selected using a recombinant rabies virus expressing glycoprotein from RABV, MOKV and WCBV. These clones bind whole virus and/or bind glycoprotein from RABV, MOKV and WCBV. Each clone includes nucleic acid sequence encoding the $V_H$ complementarity determining regions (CDRs). Identifying CDR sequences of an antibody or antibody fragment, given the nucleotide or amino acid sequence of the antibody or antibody fragment, is within the capabilities of one of skill in the art, such as by using the Kabat method (see, Kabat et al., *Sequences of Proteins of Immunological Interest*, U.S. Department of Health and Human Services, 1991; the Kabat database is now maintained online) or the International ImMunoGeneTics Information System (IMGT™, available online). Thus, also provided herein is a monoclonal antibody, or antigen-binding fragment thereof, comprising at least one CDR sequence, such as two CDR sequences or all three CDR sequences, encoded by a portion of any one of SEQ ID NOs: 1-43.

SEQ ID NOs: 44-110 represent the nucleotide sequences of 67 different clones of a naïve human $V_H$ domain library that were selected by sequential panning on cell lines expressing glycoprotein from LBV, MOKV, WCBV and DUVV. CDR1, CDR2 and CDR3 sequences of each $V_H$ domain clone are provided in Table 2. Thus, provided herein is a monoclonal antibody, or antigen-binding fragment thereof, comprising at least one, at least two or all three CDR sequences from any one of SEQ ID NOs: 44-110.

Also provided is an isolated monoclonal antibody, or antigen-binding fragment thereof, that specifically binds at least two different lyssaviruses; or that specifically binds recombinant glycoprotein from at least two different lyssaviruses. In some embodiments, the $V_H$ domain of the antibody is encoded by a nucleotide sequence at least 85%, at least 90%, at least 95%, at least 96%, at least 97%, at least 98% or at least 99% identical to the nucleotide sequence of any one of SEQ ID NOs: 1-110. In some embodiments, the $V_H$ domain of the antibody is encoded by a nucleotide sequence comprising any one of SEQ ID NOs: 1-110. In some embodiments, the at least two lyssaviruses are selected from RABV, MOKV, WCBV, LBV and DUVV. In some examples, the isolated monoclonal antibody specifically binds RABV, MOKV and WCBV; or specifically binds recombinant glycoprotein from RABV, MOKV and WCBV. In other examples, the isolated monoclonal antibody specifically binds RABV, MOKV, WCBV and LBV; or specifically binds recombinant glycoprotein from RABV, MOKV, WCBV and LBV. In other examples, the isolated monoclonal antibody specifically binds RABV, MOKV, WCBV, LBV and DUVV; or specifically binds recombinant glycoprotein from RABV, MOKV, WCBV, LBV and DUVV. In yet other examples, the isolated monoclonal antibody specifically binds MOKV, WCBV, LBV and DUVV; or specifically binds recombinant glycoprotein from MOKV, WCBV, LBV and DUVV. In particular examples, the antibody neutralizes infectivity of the lyssaviruses.

In some embodiments, the monoclonal antibody comprises a $V_L$ domain from a rabies virus-specific antibody.

In some embodiments disclosed herein, the antibody is an IgG. In other embodiments, the antibody is an IgM. In some embodiments, the antibody is a human antibody or a humanized antibody. In some embodiments, the antibody is a Fab fragment, a Fab' fragment, a F(ab)'$_2$ fragment, a single chain Fv protein (scFv), or a disulfide stabilized Fv protein (dsFv).

Further provided herein is an isolated immunoconjugate comprising a monoclonal antibody disclosed herein and a fusion partner. In some embodiments, the fusion partner is an effector molecule, a label or a heterologous polypeptide.

Also provided are compositions comprising the monoclonal antibodies or immunoconjugates disclosed herein and a pharmaceutically acceptable carrier.

Compositions comprising more than one type of anti-rabies antibody are also provided herein. In some embodiments, the composition includes (1) a monoclonal antibody that specifically binds at least two lyssaviruses as disclosed herein, and (2) a monoclonal antibody specific for RABV or RABV glycoprotein. In some embodiments, the composition further comprises a pharmaceutically acceptable carrier.

Further provided is an isolated nucleic acid molecule encoding any one of the monoclonal antibodies disclosed herein.

Also provided is a method of treating rabies in a subject, comprising administering to the subject a monoclonal antibody or antigen-binding fragment thereof, an immunoconjugate or a composition disclosed herein.

Also provided herein is an expression vector comprising a nucleotide sequence at least 85%, at least 90%, at least 95%, at least 96%, at least 97%, at least 98% or at least 99% identical to the nucleotide sequence of any one of SEQ ID NOs: 1-110. In some embodiments, the expression vector comprises the nucleotide sequence of any one of SEQ ID NOs: 1-110. In some embodiments, the expression vector further comprises the nucleotide sequence of a $V_L$ domain from a lyssavirus-specific monoclonal antibody. In particular examples, the $V_L$ domain is from a RABV-specific monoclonal antibody. In some embodiments, the expression vector is an Fc IgG expression vector. A cell comprising an expression vectors disclosed herein is also provided. Further provided is a monoclonal antibody encoded by the Fc IgG expression vector. A monoclonal antibody expressed from such an Fc IgG expression vector can be used for rabies prophylaxis and clinical rabies treatment.

IV. Lyssavirus

The genus Lyssavirus is a member of the Rhabdoviridae family within the order Mononegavirales (viruses with a single-stranded, negative sense genome). Lyssaviruses are the etiological agents of rabies encephalitis in warm-blooded animals and humans (Tordo et al., "Lyssaviruses" In Fauquet et al. eds. *Virus taxonomy: the classification and nomenclature of viruses. The 8th Report of the International Committee on Taxonomy of Viruses*. San Diego: Oxford Academic, 2006, pages 623-629; World Health Organization Expert Consultation on Rabies, 5-8 Oct. 2004, first report, World Health Organization Technical report series 931, Geneva: World Health Organization, 2005, pages 15-19). Lyssavirus species include rabies virus (RABV; genotype 1), Lagos bat virus (LBV; genotype 2), Mokola virus (MOKV; genotype 3), Duvenhage virus (DUVV; genotype 4), European bat lyssavirus-1 (EBLV-1; genotype 5), European bat lyssavirus-2 (EBLV-2; genotype 6), Australian bat lyssavirus (ABLV; genotype 7) six additional species isolated from bats: four in central Asia and Russia (Aravan virus—ARAV; Khujand virus—KHUV; Irkut virus—IRKV; and West Caucasian bat virus—WCBV), one in Africa (Shimoni bat virus—SHIBV) and one in Europe (Bokeloh bat lyssavirus—BBLV) (Kuzmin et al., *Emerg. Infect. Dis.* 14(12):1887-1889, 2008; Weyer et al., *Epidemiol. Infect.* 136:670-678, 2007; Kuzmin et al., *Virus Res.* 149(2):197-210, 2010; Freuling et al., *Emerg. Infect. Dis.* 17(8):1519-22, 2011; Kuzmin and Rupprecht, "Bat rabies" In Rabies, 2nd Edition, New York, Academic Press, 2007, pages 259-307, Jackson and Wunner, eds.).

Based on phylogeny, immunogenicity and virulence of lyssavirus isolates, two lyssavirus phylogroups have been proposed (Badrane et al., *J. Virol.* 75:3268-3276, 2001). The division into phylogroups generally correlates with the pattern of vaccine cross-protection observed for lyssaviruses (Badrane et al., *J. Virol.* 75:3268-3276, 2001; Hanlon et al., *Virus Res.* 111:44-54, 2005; Nel et al., *Expert Rev. Vaccines* 4:553-540, 2005). Phylogroup1 includes genotypes 1, 4, 5, 6 and 7, as well as ARAV, KHUV IRKV and BBLV (Kuzmin et al., *Virus Res.* 97:65-79, 2003; Kuzmin et al., *Virus Res.* 111:28-43, 2005; Hanlon et al., *Virus Res.* 111:44-54, 2005; Freuling et al., *Emerg. Infect. Dis.* 17(8):1519-22, 2011). Currently available commercial vaccines and biologicals are considered to be effective against infections of viruses from this phylogroup (Nel et al., *Expert Rev. Vaccines* 4:553-540, 2005). However, these vaccines and biologics for rabies do not offer full protection against infection with viruses outside of lyssavirus phylogroup 1 (i.e., genotypes 2, 3 and SHIBV). In addition, WCBV is recognized as the most divergent lyssavirus and exhibits limited relatedness to genotype 2 and 3 viruses. Previous studies have demonstrated little or no cross-neutralization of anti-RABV sera with WCBV (Botvinkin et al., *Emerg. Infect. Dis.* 9:1623-1625, 2003; Hanlon et al., *Virus Res.* 111:44-54, 2005).

Lyssaviruses are composed of two major structural components, a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins, the trans-membrane glycoprotein (G) and the matrix (M) protein, located at the inner side of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RABV pathogenicity was attributed to multigenic events (Yamada et al., *Microbiol. Immunol.* 50:25-32, 2006). For example, some positions in the RABV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RABV transcription and replication.

The G protein, also referred to as spike protein, is involved in cell attachment and membrane fusion of RABV. The amino acid region at position 330 to 340 (referred to as antigenic site III) of the G protein has been identified as important for virulence of certain strains of RABV. Several studies support the concept that the pathogenicity of fixed RABV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virology* 172: 206-212, 1989).

This phenomenon seems to apply at least to fixed rabies viruses such as CVS, ERA, PV, SAD-B19 and HEP-Flury strains (Anilionis et al., *Nature* 294:275-278, 1981; Morimoto et al., *Virology* 173:465-477, 1989). For example, rabies vaccine viruses possessing an amino acid differing from Arg at position 333 of the glycoprotein are described, for instance, in PCT Publication No. WO 00/32755 (describing RABV mutants in which all three nucleotides in the G protein $Arg_{333}$ codon are altered compared to the parent virus, such that the Arg at position 333 is substituted with another amino acid); European Patent No. 350398 (describing an avirulent RABV mutant SAG1 derived from the Bern SAD strain of RABV, in which the Arg at position 333 of the glycoprotein has been substituted to Ser); and European patent application 583998 (describing an attenuated RABV mutant, SAG2, in which the Arg at position 333 in the G protein has been substituted by Glu).

Other strains, such as the RC-HL strain, possess an arginine residue at position 333 of the G, but do not cause lethal infection in adult mice (Ito et al., *Microl. Immunol.* 38:479-482, 1994; Ito et al., *J. Virol.* 75:9121-9128, 2001). As such, the entire G may contribute to the virulence of RABV, although the determinants or regions have not been fully elucidated.

The G gene encodes the only protein that induces viral neutralizing antibody. At least three states of RABV glycoprotein are known: the native state (N) being responsible for receptor binding; an active hydrophobic state (A) necessary in the initial step in membrane fusion process (Gaudin, *J. Cell Biol.* 150:601-612, 2000), and a fusion inactive conformation (I). Correct folding and maturation of the G protein play important roles for immune recognition. The three potential glycosylated positions in ERA G extracellular domain occur at $Asn^{37}$, $Asn^{247}$ and $Asn^{319}$ residues (Wojczyk et al., *Glycobiology.* 8: 121-130, 1998). Nonglycosylation of G not only affects conformation, but also inhibits presentation of the protein at the cell surface.

V. Antibody Compositions and Therapeutic Methods

Standard treatment for post-exposure rabies prophylaxis includes thorough wound-washing with soap and water followed by administration of vaccine and anti-rabies virus immunoglobulin (RIG) of human or equine origin. RIG administered shortly after exposure at the wound site provides passive immunity which neutralizes rabies virus and prevents its spread until the patient's immune response following vaccination is elicited. Deaths due to post-exposure prophylaxis failure are most commonly attributed to deviations from the recommended regimen such as late initiation of post-exposure prophylaxis or no administration of RIG (Wilde, *Vaccine,* 25:7605-7609, 2007). Provided herein are human monoclonal antibodies that specifically bind at least two different lyssaviruses. Thus, the disclosed antibodies are useful for the treatment of clinical rabies and/or for post-exposure rabies prophylaxis.

Compositions are provided that include a monoclonal antibody, or antigen-binding fragment thereof, that specifically binds at least two different lyssaviruses (such as whole virus or lyssavirus glycoprotein, or both). Compositions comprising immunoconjugates or immunotoxins are also provided. The compositions can be prepared in unit dosage forms for administration to a subject. The amount and timing of administration are at the discretion of the treating physician to achieve the desired purposes. For example, the compositions can be administered to a subject exhibiting clinical signs of rabies, or can be administered to a subject that has been exposed to or bitten by a rabid animal (or an animal suspected of being rabid). The antibody can be formulated for systemic or local (such as at a wound site) administration.

The compositions for administration can include a solution of the antibody (or antigen-binding fragment thereof) that specifically binds lyssavirus dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

Doses of lyssavirus mAb generally range from about 1 to about 50 IU/kg, such as about 5 to about 40 IU/kg, or about 5 to about 20 IU/kg. In particular examples, the dose is about 5 IU/kg, about 10 IU/kg or about 20 IU/kg. However, the dose of lyssavirus mAb will vary depending upon the antibody (or antibody cocktail) selected and the particular subject to be treated. An appropriate does can be determined by a medical practitioner.

Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies may be provided in lyophilized form and rehydrated with sterile water before administration, although they are also provided in sterile solutions of known concentration. Antibodies can be administered by slow infusion, or by intravenous push or bolus. Antibody compositions can also be administered topically.

The antibody that specifically binds lyssavirus can be administered to prevent the development of rabies disease and/or slow the spread of lyssavirus from a wound site to distant sites in the body. In these applications, a therapeutically effective amount of an antibody is administered to a subject in an amount sufficient to inhibit virus replication or spread, or to inhibit a sign or a symptom of rabies. Suitable subjects may include those diagnosed with rabies, or subjects recently exposed to (such as bitten by) animal infected with a lyssavirus, or suspected of being infected with a lyssavirus.

A therapeutically effective amount of a lyssavirus-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with other therapeutic agents (such as a rabies vaccine), either simultaneously or sequentially.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

The following examples are provided to illustrate certain particular features and/or embodiments. These examples should not be construed to limit the disclosure to the particular features or embodiments described.

EXAMPLES

Example 1

Construction and Characterization of Recombinant Rabies Virus with Three Glycoprotein Genes This example describes the generation and characterization of a recombinant ERA strain rabies virus encoding three different glycoprotein genes. The recombinant virus, referred to as ERA-3G, comprises rabies virus (RABV) glycoprotein, Mokola virus (MOKV) glycoprotein and West Caucasian bat virus (WCBV) glycoprotein. The cloning strategy for ERA-3G is shown in FIG. 1. The rabies virus reverse genetics system used to generate this virus in described in detail in PCT Publication No. WO 2007/047459. ERA-3G includes the attenuating mutation in the RABV glycoprotein gene that results in an arginine to glutamic acid change at amino acid residue 333 of the protein.

The G genes from MOKV and WCBV were cloned into the ERA backbone (see SEQ ID NO: 7 of PCT Publication No. WO 2007/047459) by RT-PCR using viral genomic RNA from virus-infected cells as template. The following primers were used for amplification of the glycoprotein genes:

```
                                         (SEQ ID NO: 111)
MokolaG5-CGACTGCAGATGAATATACCTTGCTTTGTTGTGATTC (SEQ ID NO: 112)
MokolaG3-CGTGGTACCTCATGTACCTGGAAGCCCTTTATAGGACTC (SEQ ID NO: 113)
WCBVG5-CATCTGCTAGCAATGGCTTCCTACTTTGCGTTG (SEQ ID NO: 114)
WCBVG3-TTCAATGGTACCTTATTGGGCAGTTTGTCCCTT
```

The amplified G genes for MOKV (SEQ ID NO: 115) and WCBV (SEQ ID NO: 116) were confirmed by sequencing. Two extra transcription units were synthesized (each with the sequence of SEQ ID NO: 117) and introduced into the gene junctions between the phosphoprotein (P) and the matrix protein (M), and the G and the RNA dependent RNA polymerase (L) (FIG. 1). The MOKV G was cloned into the gene junction between the P and M, and WCBV G into the gene junction between the G and L in the ERA genome backbone.

Recombinant virus was recovered by transfection of the above described construct into BSR cells using the method described in PCT Publication No. WO 2007/047459.

Example 2

Identification of Domain Antibodies Specific for Lyssaviruses

Current anti-rabies immune globulins do not neutralize all lyssaviruses. The use of immunized humans for immune library construction biases libraries towards neutralization of RABV genotype 1 with lower cross-reactivity towards other Lyssavirus genotypes. One method to circumvent this limitation is selecting monoclonal antibodies (mAbs) from naïve immune libraries, which theoretically contain binders to any antigen.

This example describes the use of a naïve, human-heavy domain, phage display library (Famm et al., *J. Mol. Biol.* 376:926-931, 2008) to identify and characterize novel anti-Lyssavirus mAbs. The phage display library ($3 \times 10^9$ clones) is based on human $V_H$ framework with diversity introduced into CDR1, CDR2 and CDR3 by PCR mutagenesis. The library was panned using a recombinant ERA RABV expressing three different G proteins (see Example 1)—the G proteins from rabies virus (RABV), Mokola virus (MOKV) and West Caucasian Bat virus (WCBV)—following established methods (Kramer et al., *Eur. J. Immunol.* 35:2131-2145, 2005; Lee et al., *Nat. Protoc.* 2:3001-3008, 2007).

Library Panning

For the first two times the library was panned, either purified G protein or whole virus was used to select binders for three rounds and then switched antigens for three more rounds so that binders selected for G protein were then panned against whole virus and vice versa. After the last round of selection, 552 individual clones were picked (276 from each panning scheme) and potential high affinity domain antibodies (dAb) were identified by ELISA.

ELISA

The ELISA procedure was standardized using the soluble dAb fragments from these clones and the same antigens used to pan the library. Approximately 5-10% of selected clones bind to the original antigen and 2-3% bind to the secondary antigen (Table 1).

TABLE 1

Results of Panning Phage Display Library

| Scheme | Screened | Binding* whole virus | Binding* G protein |
|---|---|---|---|
| Whole virus→G Protein | 276 | 30 (10.9%) | 4 (1.4%) |
| G Protein→Whole virus | 276 | 8 (2.9%) | 13 (4.7%) |
| Total | 552 | 38 (6.9%) | 17 (3.1%) |

Figure 3:
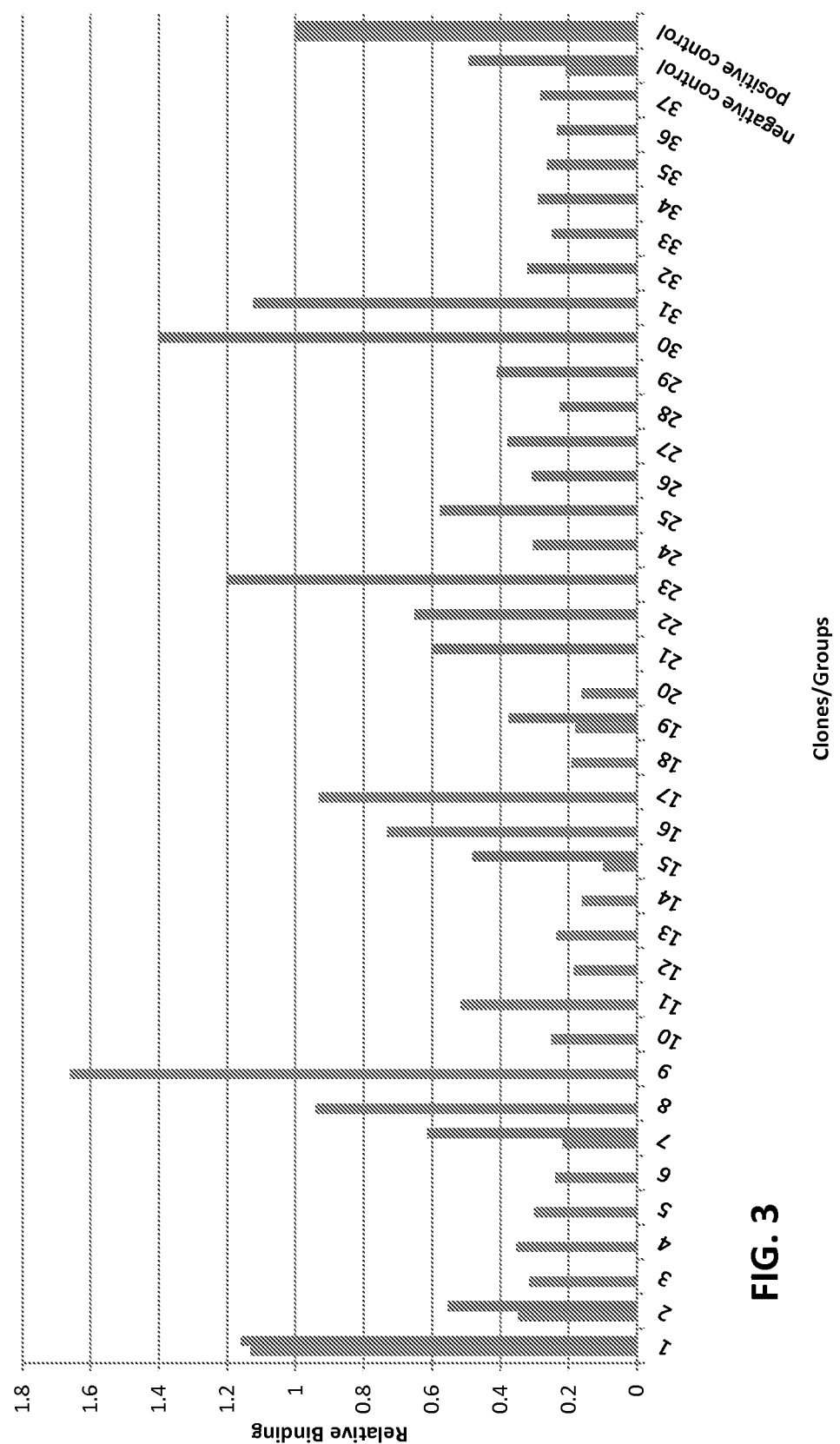
FIG. 3: Results of glycoprotein ELISA. Relative binding of selected human variable heavy ($V_H$) domain phage display clones to glycoproteins purified from recombinant ERA RABV expressing glycoprotein (G) from RABV, MOKV and WCBV. Left bars for each clone indicate clones selected using the whole recombinant virus ERA RABV expressing glycoprotein (G) from RABV, MOKV and WCBV. Right bars for each clone indicate clones selected using glycoproteins purified from the recombinant ERA RABV expressing glycoprotein (G) from RABV, MOKV and WCBV. Using a standard ELISA method, raw absorbance (420 nm-650 nm) was fixed relative to a known clone binding to its cognate antigen (positive control).
Figure 4:
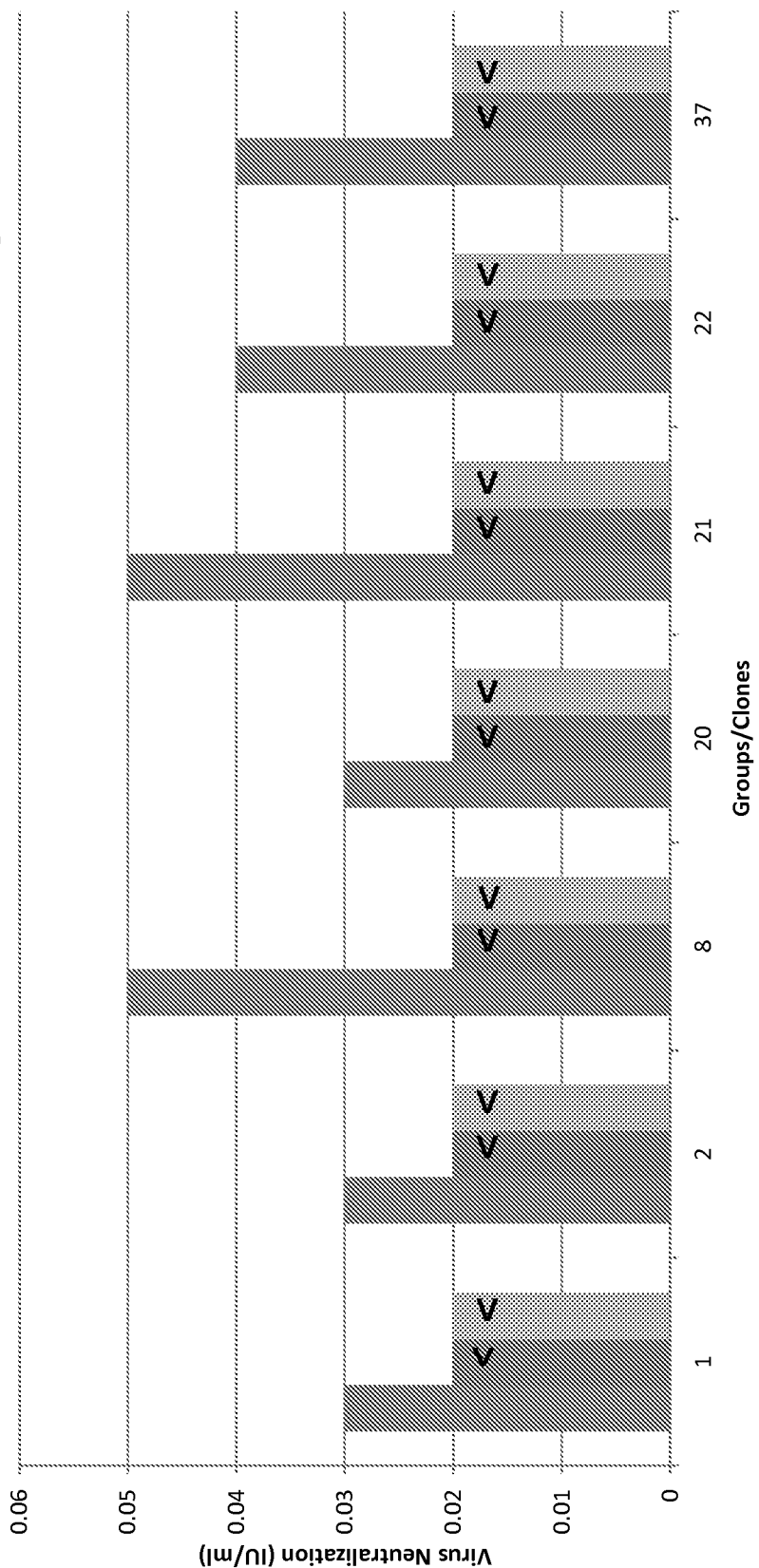
FIG. 4: Results of rapid fluorescent focus inhibition test (RFFIT). Rabies virus ERA3G was incubated with standard dilutions of soluble domain antibodies from selected clones for 20 hours. Virus neutralization was assessed using direct immunofluorescent staining. Results of three biological replicates are shown with titers less than 0.02 IU/ml indicated by the symbol (<).

*Number of clones with mean ELISA binding ≥ positive control from three biological replicates Relative binding (as assessed by ELISA) of each of the clones to whole virus and glycoprotein is shown in FIG. 2 and FIG. 3, respectively. Representative clones from groups 1 and 17 appear to bind to whole virus, whereas clones from groups 1, 9, 23, 30 and 31 appear to bind glycoprotein. A modified rapid fluorescent focus inhibition test (RFFIT) was used to screen dAbs for virus neutralization. The results are shown in FIG. 4. Observed weak neutralization may be due to poor expression of soluble antibodies due to in-frame stop codons.

Sequencing of Clones

Sixty-nine percent of the clones selected for binding to whole virus and 37% of the clones selected for binding to glycoprotein were successfully sequenced. The sequences of each clone are provided in the Sequence Listing as SEQ ID NOs: 1-43 as follows:

| Clone | SEQ ID NO: |
|---|---|
| H01_plate2_group1 | 1 |
| B05_plate4_group2 | 2 |
| B08_plate4_group3 | 3 |
| C10_plate4_group4 | 4 |
| G05_plate2_group5 | 5 |
| G04_plate2_group6 | 6 |
| C02_plate4_group7 | 7 |
| A06_plate4_group8 | 8 |
| H12_plate1_group9 | 9 |
| F09_palte4_group10 | 10 |
| H09_plate4_group11 | 11 |
| G04_plate4_group12 | 12 |
| F05_plate4_group13 | 13 |
| E01_plate2_group14 | 14 |
| E07_plate2_group15 | 15 |
| F03_plate1_group16 | 16 |
| E02_plate2_group17 | 17 |
| A05_plate1_group18 | 18 |
| C08_plate1_group19 | 19 |
| B02_plate1_group20 | 20 |
| G09_plate11_group1 | 21 |
| H07_plate14_group2 | 22 |
| E04_plate11_group7 | 23 |
| H08_plate13_group15 | 24 |

-continued

| Clone | SEQ ID NO: |
|---|---|
| F12_plate13_group18 | 25 |
| B03_plate14_group19 | 26 |
| H05_plate13_group21 | 27 |
| G06_plate14_group22 | 28 |
| F05_plate11_group23 | 29 |
| D11_plate11_group24 | 30 |
| H01_plate13_group25 | 31 |
| C10_plate11_group26 | 32 |
| D11_plate14_group27 | 33 |
| B08_plate11_group28 | 34 |
| H08_plate14_group29 | 35 |
| H06_plate14_group30 | 36 |
| H07_plate11_group31 | 37 |
| E12_plate14_group32 | 38 |
| A11_plate11_group33 | 39 |
| B04_plate13_group34 | 40 |
| A08_plate11_group35 | 41 |
| B05_plate13_group36 | 42 |
| E04_plate14_group37 | 43 |

Example 3

Lyssavirus Domain Antibodies Selected by Sequential Panning of Glycoprotein Expressing Cells This example describes the identification of $V_H$ domain antibodies specific for lyssavirus glycoprotein by sequential panning of a naïve, human $V_H$ domain phage display library (Famm et al., *J. Mol. Biol.* 376:926-931, 2008) on cell lines expressing glycoprotein (G) from several different lyssaviruses.

Flp-In-BHK cells (Invitrogen) were transfected with a pEF5/FRT/V5 plasmid (Invitrogen) encoding glycoprotein from LBV (SEQ ID NO: 118), MOKV (SEQ ID NO: 115), WCBV (SEQ ID NO: 116), or DUVV (SEQ ID NO: 119). The library was panned sequentially on cells that express LBV G protein, followed by MOKV G protein, followed by WCBV G protein and finally DUVV G protein. Selection on cells was carried out using the method described by Lee et al. (*Nature Protocols* 2(11):3001-3008, 2007).

Using this method, 67 unique nucleotide sequences were identified (Table 2). Each $V_H$ sequence has at least one change in amino acid sequence when translated. In-frame "TAG" (stop codons) will be changed to "GAG" (glutamate codons) to allow expression in eukaryotic cell line. $V_H$ sequences will be cloned into the pEF5/FRT/V5 plasmid to transfect Flp-In-BHK cells for expression of antibodies.

TABLE 2

Unique $V_H$ clones identified by sequential panning of cells

| $V_H$ Clone Name | SEQ ID NO: | CDR1 nucleotide positions[1] | CDR2 nucleotide positions[1] | CDR2 nucleotide positions[1] |
|---|---|---|---|---|
| plate11_G09_group1 | 44 | 76-111 | 148-193 | 295-336 |
| plate14_H07_group2 | 45 | 76-111 | 148-193 | 295-336 |
| plate4_B08_group3 | 46 | 76-111 | 148-193 | 295-330 |
| plate4_C10_group4 | 47 | 76-111 | 148-193 | 295-333 |
| plate2_G05_group5 | 48 | 76-111 | 148-193 | 295-351 |
| plate2_G04_group6 | 49 | 76-111 | 148-193 | 295-339 |
| plate4_C02_group7 | 50 | 76-111 | 148-193 | 295-339 |
| plate4_A06_group8 | 51 | 76-111 | 148-193 | 295-351 |
| plate1_H12_group9 | 52 | 76-111 | 148-193 | 295-339 |
| palte4_F09_group10 | 53 | 76-111 | 148-193 | 295-336 |
| plate4_H09_group11 | 54 | 76-111 | 148-193 | 295-333 |
| plate4_G04_group12 | 55 | 76-111 | 148-193 | 295-342 |
| plate4_F05_group13 | 56 | 76-111 | 148-193 | 295-354 |
| plate2_E01_group14 | 57 | 76-111 | 148-193 | 295-360 |
| plate13_H08_group15 | 58 | 76-111 | 148-193 | 295-348 |
| plate4_B05_group16 | 59 | 76-111 | 148-193 | 295-336 |
| plate2_E02_group17 | 60 | 76-111 | 148-193 | 295-336 |
| plate1_A05_group18 | 61 | 76-111 | 148-193 | 295-336 |
| plate14_B03_group19 | 62 | 76-111 | 148-193 | 295-333 |
| plate1_B02_group20 | 63 | 76-111 | 148-193 | 295-351 |
| plate13_F12_group21 | 64 | 76-111 | 148-193 | 295-336 |
| plate14_G06_group22 | 65 | 76-111 | 148-193 | 295-351 |
| plate11_F05_group23 | 66 | 76-111 | 148-193 | 295-339 |
| plate11_D11_group24 | 67 | 76-111 | 148-193 | 295-330 |
| plate13_H01_group25 | 68 | 76-111 | 148-193 | 295-339 |
| plate11_C10_group26 | 69 | 76-111 | 148-193 | 295-336 |
| plate14_D11_group27 | 70 | 76-111 | 148-193 | 295-330 |
| plate11_B08_group28 | 71 | 76-111 | 148-193 | 295-330 |
| plate14_H08_group29 | 72 | 76-111 | 148-193 | 295-330 |
| plate14_H06_group30 | 73 | 76-111 | 148-193 | 295-345 |
| plate11_H07_group31 | 74 | 76-111 | 148-193 | 295-333 |
| plate14_E12_group32 | 75 | 76-111 | 148-193 | 295-336 |
| plate11_A11_group33 | 76 | 76-111 | 148-193 | 295-333 |
| plate13_B04_group34 | 77 | 76-111 | 148-193 | 295-339 |
| plate11_A08_group35 | 78 | 76-111 | 148-193 | 295-345 |
| plate13_B05_group36 | 79 | 76-111 | 148-193 | 295-333 |
| plate14_E04_group37 | 80 | 76-111 | 148-193 | 295-333 |
| plate5_B02_group38 | 81 | 76-111 | 148-193 | 295-339 |
| plate5_A08_group39 | 82 | 76-111 | 148-193 | 295-330 |
| plate5_G03_group40 | 83 | 76-111 | 148-193 | 295-339 |
| plate5_D02_group41 | 84 | 76-111 | 148-193 | 295-339 |
| plate5_B11_group42 | 85 | 76-111 | 148-193 | 295-339 |
| plate5_A05_group43 | 86 | 76-111 | 148-193 | 295-330 |
| plate5_G09_group44 | 87 | 76-111 | 148-193 | 295-339 |
| plate5_C01_group45 | 88 | 76-111 | 148-193 | 295-339 |
| plate5_D01_group46 | 89 | 76-111 | 148-193 | 295-339 |
| plate5_C10_group47 | 90 | 76-111 | 148-193 | 295-339 |
| plate5_D10_group48 | 91 | 76-111 | 148-193 | 295-339 |
| plate5_D03_group49 | 92 | 76-111 | 148-193 | 295-339 |
| plate5_C03_group50 | 93 | 76-111 | 148-193 | 295-339 |
| plate5_G10_group51 | 94 | 76-111 | 148-193 | 295-339 |
| plate5_H06_group52 | 95 | 76-111 | 148-193 | 295-330 |
| plate5_A06_group53 | 96 | 76-111 | 148-193 | 295-330 |
| plate52_E08_group54 | 97 | 10-45 | 82-127 | 229-264 |
| plate52_C06_group55 | 98 | 44-79 | 115-160 | 262-306 |
| plate52_E01_group56 | 99 | 76-111 | 148-193 | 295-330 |
| plate52_C08_group57 | 100 | 34-69 | 106-151 | 253-288 |
| plate52_B09_group58 | 101 | 12-47 | 84-129 | 231-266 |
| plate53_A03_group59 | 102 | 76-111 | 148-193 | 295-336 |
| plate53_C12_group60 | 103 | 76-111 | 148-193 | 295-330 |
| plate53_B08_group61 | 104 | 76-111 | 148-193 | 295-351 |
| plate54_A03_group62 | 105 | 73-105 | 142-187 | 289-324 |
| plate54_E11_group63 | 106 | 65-97 | 134-179 | 281-316 |
| plate54_D09_group64 | 107 | 65-97 | 134-179 | 281-316 |
| plate54_C01_group65 | 108 | 65-97 | 134-179 | 281-316 |
| plate54_G05_group66 | 109 | 60-92 | 129-174 | 276-311 |
| plate54_C12_group67 | 110 | 77-112 | 149-194 | 296-358 |

[1]Each CDR sequence is identified by the nucleotide positions of the provided SEQ ID NO.

Example 4

Rabies Prophylaxis Using Lyssavirus mAbs

A subject diagnosed with rabies or at risk of developing rabies (such as a subject bitten by a potentially rabid animal) is subjected to rabies post-exposure prophylaxis, which includes administration of a rabies vaccine, such as IMOVAX™ or RABAVERT™, according to the recommended dosing schedule. Subjects who have not previously been vaccinated against rabies will further be treated with one or more of the lyssavirus mAbs disclosed herein.

Lyssavirus mAb is administered intramuscularly to the subject at a site distant to the site of vaccine administration. If the subject diagnosed with rabies, or at risk of developing rabies, has a bite wound, lyssavirus mAb can optionally be administered directly into the wound and to the area directly adjacent to the wound.

Doses of lyssavirus mAb generally range from 1 to 50 IU/kg. In particular examples, the dose is about 5 or about 20 IU/kg. However, the dose of lyssavirus mAb will vary depending upon the antibody (or antibody cocktail) selected and the particular subject to be treated. An appropriate does can be determined by a medical practitioner.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of identifying a monoclonal antibody, or antigen-binding fragment thereof, that specifically binds at least two different lyssavirus species, comprising:

screening a naïve antibody phage display library with at least two different cell lines, wherein each cell line expresses a different lyssavirus glycoprotein selected from the RABV glycoprotein, the MOKV glycoprotein, the WCBV glycoprotein, the LBV glycoprotein and the DUVV glycoprotein, and wherein the phage display library is screened sequentially on the at least two different cell lines; and selecting a phage display clone that specifically binds to at least two different lyssavirus species, glycoproteins from at least two different lyssavirus species, or both, thereby identifying a monoclonal antibody, or antigen-binding fragment thereof, that specifically binds at least two different lyssavirus species.

2. The method of claim 1, wherein the phage display library is a naïve human $V_H$ domain library.

3. The method of claim 1, wherein the antigen-binding fragment comprises a $V_H$ domain.

4. The method of claim 3, further comprising cloning the antigen-binding fragment comprising the $V_H$ domain into an IgG expression vector.

5. The method of claim 4, wherein the IgG expression vector further comprises a nucleic acid sequence encoding a variable light ($V_L$) domain from a rabies virus-specific antibody.

6. The method of claim 1, wherein the selecting step comprises an ELISA to detect specific binding to lyssavirus glycoprotein, whole virus, or both.

7. The method of claim 1, further comprising screening the selected phage display clone for lyssavirus neutralization.

* * * * *

SEQUENCE LISTING

```
<160> NUMBER OF SEQ ID NOS: 119

<210> SEQ ID NO 1
<211> LENGTH: 822
<212> TYPE: DNA
<213> ORGANISM: Artificial Sequence
<220> FEATURE:
<223> OTHER INFORMATION: Recombinant polynucleotide

<400> SEQUENCE: 1
taaacaactt tcaacagtct atgtttgccc cctttccaag tcggttcatc tctatgtctg      60
tataatgtgc ggccgaattc agatcctctt ctgagatgag tttttgttct gcggccgcgc     120
tcgagacggt gaccagggtt ccctgacccc aaaacttgaa cttgttcgga aacgacaacc     180
gcctctaact cgcgcaataa tataccgcgg tgtcctcggc acgcaggctg ttcatttgca     240
gatacagcgt gttcttggaa ttgtcacggg agatggtgaa ccggccttc acggagtctg      300 cgtagtatgt gctaccgcta cgcatcccaa tgcttgatac ccactctaga cccttccctg     360
gagcctggcg gacccaggcc atattctaat ggctaatctt aactccggag gctgcacagg     420
agagacgaag ggaccccca ggctgtacca agcctccccc agactccaac agctgcacct      480
gggccatggc cggctgggcc gcatagaaag gtaccactaa aggaattgcg aataataatt     540
ttttcattat gactgtctcc ttgaaataga atttgcatgc aagcttggcg taatcatggt     600
catagctgtt tcctgtgtga aattgttatc cgctcacaat tccacacaac atacgagccg     660
gaagcataaa gtgtaaagcc tggggtgcc taatgagtga gctaactcac attaatttgc      720
gtttgcgctc actgcccgct tttccagtcc gggaaacctg tcgtgcccag ctgcattaat     780
gaatcggcca accgcgcggg gagaggcggt ttgcgtattg gg                         822

<210> SEQ ID NO 2
<211> LENGTH: 663
<212> TYPE: DNA
<213> ORGANISM: Artificial Sequence
<220> FEATURE:
<223> OTHER INFORMATION: Recombinant polynucleotide

<400> SEQUENCE: 2
cagtcggttc atctctatgt ctgtttaatg tgcggccgaa ttcagatcct cttctgagat      60 gagttttttgt tctgcggccg cgctcgagac ggtgaccagg gttccctgac cccaaaactg     120
gacggtcgtc ggacgcatat actaccgacc tctcgcgcaa tgatataccg cggtgtcctc     180
ggcacgcagg ctgttcattt gcagatacag cgtgttcttg gaattgtcac gggagatggt     240
gaaccggccc ttcacggagt ctgcgtagta tgtgctaccg tcacgccac gaatgcttga      300 tacccactct agacccttcc ctggagcctg gcggaccag cccatattct tatgggtaag     360
cctaactccg gaggctgcac aggagagacg cagggacccc ccaggctgta ccaagccttc     420
cccagactcc aacagctgca cctgggccat ggccggctgg gccgcataga aaggtaccac     480
```

```
taaaggaatt gcgaataata attttttcat tatgactgtc tccttgaaat agaatttgca      540
tgcaagcttg gcgtattcat ggtcatagct gtttcctgtg tgaaattgtt atccgctcac      600
aattccacac aacatacgag ccggaagcat aaagtgtaaa gcctgtggtg cctaatgagt      660
gag                                                                    663

<210> SEQ ID NO 3
<211> LENGTH: 649
<212> TYPE: DNA
<213> ORGANISM: Artificial Sequence
<220> FEATURE:
<223> OTHER INFORMATION: Recombinant polynucleotide

<400> SEQUENCE: 3
acagtctatg cggccccctt tccagtcggt tcatctctat gtctgtataa tgtgcggccg       60
aattcagatc ctcttctgag atgagttttt gttctgcggc cgcgctcgag acggtgacca      120
gggttccctg accccaatag cggaagttgg cggtacgcct cctcctaccc gcgcaataat      180
ataccgcggt gtcctcggca cgcaggctgt tcatttgcag atacagcgtg ttcttggaat      240
tgtcacggga gatggtgaac cggcccttca cggagtctgc gtattatgtg ctaccgcttc      300
gcgtacgaat ggttgatacc cactctagac ccttccctgg agcctggcgg acccaggcca      360
tatcctaata gataatgtta actccggagg ctgcacagga gagacgcagg gacccccag       420 gctgtaccaa gcctccccca gactccaaca gctgcacctg ggccatggcc ggctgggccg      480
catagaaagg taccactaaa ggaattgcga ataataattt tttcattatg actgtctcct      540
tgaaatagaa tttgcatgca agcttggcgt aatcatggtc atagctgttt cctgtgtgaa      600
attgttatct cgctcacaat tccacacaac atacgagccg gaagcataa                  649

<210> SEQ ID NO 4
<211> LENGTH: 780
<212> TYPE: DNA
<213> ORGANISM: Artificial Sequence
<220> FEATURE:
<223> OTHER INFORMATION: Recombinant polynucleotide

<400> SEQUENCE: 4
aaacaacttt caacagtcta tgcggccccc tttccaagtc ggttcatctc tatgtctgta       60
taatgtgcgg ccgaattcag atcctcttct gagatgagtt tttgttctgc ggccgcgctc      120
gagacggtga ccagggttcc ctgaccccaa tacttcatgt tcgccggccg cctaaccctc      180
gttgtcgcgc aataatatac cgcggtgtcc tcggcacgca ggctgttcat ttgcagatac      240
agcgtgttct tggaattgtc acgggagatg gtgaaccggc ccttcacgga gtctgcgtag      300
tatgtgctac cgttttgcat cagaatgctt gataccact ctagaccctt ccctggagcc      360
tggcggaccc aggccataga ctaatagcta atcttaactc cggaggctgc acaggagaga      420
cgcagggacc cccaggctg taccaagcct cccccagact ccaacagctg cacctgggcc      480
atggccggct gggccgcata gaaaggtacc actaaaggaa ttgcgaataa taattttttc      540
attatgactg tctccttgaa atagaatttg catgcaagct tggcgtaaat catggtcata      600
gctgtttcct gtgtgaaaat tgttatccgc tcacaattcc acacaacata cgagcccgga      660
agcataaagt gtaaagcctg gggtgcctaa tgagtgagct aaccccacat ttaattgctt      720
tgcgctcact gcccccttc cattcgggaa acctgtcgtg ccagctgcat taatgaaatc      780

<210> SEQ ID NO 5
<211> LENGTH: 799
```

-continued

<212> TYPE: DNA
<213> ORGANISM: Artificial Sequence
<220> FEATURE:
<223> OTHER INFORMATION: Recombinant polynucleotide

<400> SEQUENCE: 5

| | | | | | |
|---|---|---|---|---|---|
| taaacaactt | tcaacagtct | atgcggcccc | ctttccaagt | cggttcatct | ctatgtctgt | 60 |
| ataatgtgcg | gccgaattca | gatcctcttc | tgagatgagt | ttttgttctg | cggccgcgct | 120 |
| cgagacggtg | accagggttc | cctgacccca | atacctgatc | ggcttcgcag | tcagaccagc | 180 |
| ccaccacata | ctcctaggaa | ctgtcgcgca | ataatatacc | gcggtgtcct | cggcacgcag | 240 |
| gctgttcatt | tgcagataca | gcgtgttctt | ggaattgtca | cggagatgg | tgaaccggcc | 300 |
| cttcacggag | tctgcgtagt | atgtgctacc | gcctcgcata | ttaatgcttg | atacccactc | 360 |
| tagacccttc | cctggagcct | ggcggaccca | gcccatagcc | taagagttaa | acctatatcc | 420 |
| ggaggctgca | caggagagac | gcagggaccc | ccaggctgt | accaagcctc | ccccagactc | 480 |
| caacagctgc | acctgggcca | tggccggctg | ggccgcatag | aaaggtacca | ctaaaggaat | 540 |
| tgcgaataat | aattttttca | ttatgactgt | ctccttgaaa | tagaatttgc | atgcaagctt | 600 |
| ggcgtaatca | tggtcatagc | tgtttcctgt | gtgaaattgt | tatccgctca | caattcccca | 660 |
| caacatacga | gcccggaagc | ataaagtgta | aagccctggg | gtgcctaatg | agtgagctaa | 720 |
| ctcacattta | attgcgttgc | gctcactgcc | cgcttttcca | gtcgggaaac | cctgtcgtgc | 780 |
| cagcttgcat | taatgaatc | | | | | 799 |

<210> SEQ ID NO 6
<211> LENGTH: 838
<212> TYPE: DNA
<213> ORGANISM: Artificial Sequence
<220> FEATURE:
<223> OTHER INFORMATION: Recombinant polynucleotide

<400> SEQUENCE: 6

| | | | | | |
|---|---|---|---|---|---|
| tgaattttt | ctgttatgag | gtttccgcta | aacaactttc | aacagtctat | gcggccccct | 60 |
| ttccaagtcg | gttcatctct | atgtctgtat | aatgtgcggc | cgaattcaga | tcctcttctg | 120 |
| agatgagttt | ttgttctgcg | gccgcgctcg | agacggtgac | cagggttccc | tgaccccaat | 180 |
| accggagcgg | cgacacaagc | caccgcttac | cacgcctacc | cgcgcaataa | tataccgcgg | 240 |
| tgtcctcggc | acgcaggctg | ttcatttgca | gatacagcgt | gttcttggaa | ttgtcacggg | 300 |
| agatggtgaa | ccggcccttc | acggagtctg | cgtagtatgt | gctaccgctt | gcgtcataa | 360 |
| tgcttgatac | ccactctaga | cccttccctg | gagcctggcg | acccagccc | atatactaat | 420 |
| tggtaaactt | aactccggag | gctgcacagg | agagacgcag | ggaccccca | ggctgtacca | 480 |
| agcctcccc | agactccaac | agctgcacct | gggccatggc | cggctgggcc | gcatagaaag | 540 |
| gtaccactaa | aggaattgcg | aataataatt | ttttcattat | gactgtctcc | ttgaaataga | 600 |
| atttgcatgc | cagcttggcg | taatcatggt | catagctgtt | ccctgtgtga | aatttgttat | 660 |
| ccgctcacaa | ttccacacaa | catacgagcc | ggaagcataa | aagtgtaaag | cctggggtgc | 720 |
| ctaatgagtg | agctaactca | cattaattgc | gttgcgctca | ctgcccgctt | tccagtcggg | 780 |
| aaacctgtcg | cgccagcctg | catttaatga | atcggccaac | gcgcgggag | aggcggtt | 838 |

<210> SEQ ID NO 7
<211> LENGTH: 673
<212> TYPE: DNA
<213> ORGANISM: Artificial Sequence
<220> FEATURE:

<223> OTHER INFORMATION: Recombinant polynucleotide

<400> SEQUENCE: 7

```
agtcggttca tctctatgtc tgtataatgt gcggccgaat tcagatcctc ttctgagatg      60
agttttgtt ctgcggccgc gctcgagacg gtgaccaggg ttccctgacc ccaaaacttg     120
atgtacttcg tacgaaaagg cgcccgacgc gcactcgcgc aataatatac gcggtgtcc     180
tcggcacgca ggctgttcat ttgcagatac agcgtgttct tggaattgtc acggagatg     240
gtgaaccggc ccttcacgga gtctgcgtag tatgtgctac cgcttcggct attaatgcct    300
gatacccact ctagaccctt ccctggagcc tggcggaccc agctcataaa ctaatggtta    360
aacctaactc cggaggctgc acaggagaga cgcagggacc ccccaggctg taccaagcct    420
cccccagact ccaacagctg cacctgggcc atggccggct gggccgcata gaaaggtacc    480
actaaaggaa ttgcgaataa taattttttc attatgactg tctccttgaa atagaatttg    540
catgcaagct tggcgtaatc atggtcatag ctgtttcctg tgtgaaattg ttatccgctc    600
acaattccac acaacatacg agccggaagc ataaagtgta aagcctgggg tgcctaatga    660
gtgagctaac ttc                                                        673
```

<210> SEQ ID NO 8
<211> LENGTH: 649
<212> TYPE: DNA
<213> ORGANISM: Artificial Sequence
<220> FEATURE:
<223> OTHER INFORMATION: Recombinant polynucleotide

<400> SEQUENCE: 8

```
gccgaattca gatcctcttc tgagatgagt ttttgttctg cggccgcgct cgagacggtg     60
accagggttc cctgacccca aaccccatc ttgtggggca cagaccaagg cctacccctc    120
aaacgccgag gtgccgcgca ataatatacc gcggtgtcct cggcacgcag gctgttcatt    180
tgcagataca gcgtgttctt ggaattgtca cgggagatgg tgaaccggcc cttcacggag    240
tctgcgtagt atgtgctacc gtctgtggta ttaatgcctg atacccactc tagacccttc    300
cctggagcct gcggaccca gctcatagcc taattgctaa acctatctcc ggaggctgca    360
caggagagac gcagggaccc cccaggctgt accaagcctc cccagactc aacagctgc     420
acctgggcca tggccggctg ggccgcatag aaaggtacta ctaaaggaat tgcgaataat    480
aatttttttca ttatgactgt ctccttgaaa tagaatttgc atgcaagctt ggcgtaatta    540
tggtcatagc tgttttccct gtgtgaaatt gttatccgct cacaattcca cacaacatac    600
gagctcggaa gcataaagtg tataagcctg ggtgcctaat gagtgagct                649
```

<210> SEQ ID NO 9
<211> LENGTH: 866
<212> TYPE: DNA
<213> ORGANISM: Artificial Sequence
<220> FEATURE:
<223> OTHER INFORMATION: Recombinant polynucleotide

<400> SEQUENCE: 9

```
aaatgaattt tctgtatgag gttttgctaa acaactttca acagtctatg cggcccctt      60
tccagtcggt tcatctctat gtctgtataa tgtgcggccg aattcagatc ctcttctgag    120
atgagttttt gttctgcggc cgcgctcgag acggtgacca gggttccctg accccaagac    180
gtcaggggct tcggccactt cctcccccca tgccatctcg cgcaataata taccgcggtg    240
tcctcggcac gcaggctgtt catttgcaga tacagcgtgt tcttggaatt gtcacgggag    300
```

```
atggtgaacc ggcccttcac ggagtctgcg tagtatgtgc taccgttagt catagcaatg      360 gttgatalccc actctagacc cttccctgga gcctggcgga cccagcccat atactaatgg      420
ctaaacctaa atccggaggc tgcacaggag agacgcaggg accccccagg ctgtaccaag      480
cctcccccag actccaacag ctgcacctgg gccatggccg gctgggccgc atagaaaggt      540
accactaaag gaattgcgaa taataatttt ttcattatga ctgtctcctt gaaatagaat      600
ttgcatgcaa gcttggcgta aatcatggtc atagctgttt cctgtgtgaa attgttatcc      660
gctcacaatt ccacacaaca tacgagccgg aagcataaag tgtaaagcct ggggtgccta      720
atgagtgagc taactcacat taattgcgtt gcgctcactg cccgctttcc gtcgggaaac      780
ctgtcgtgcc agctgcatta atgaatcggc caacgcgcg gggagaggcg gtttgcgta       840 ttgggcgctc ttccgctttc ctcgct                                          866
```

<210> SEQ ID NO 10
<211> LENGTH: 878
<212> TYPE: DNA
<213> ORGANISM: Artificial Sequence
<220> FEATURE:
<223> OTHER INFORMATION: Recombinant polynucleotide

<400> SEQUENCE: 10

```
gaattttctg tatgaggttt tgctaaacaa ctttcaacag tctatgcggc cccctttcca       60
gtcggttcat ctctatgtct gtataatgtg cggccgaatt cagatcctct tctgagatga      120
gtttttgttc tgcggccgcg ctcgagacgt gaccagggt tccctgaccc caaaaccgca      180
tgtagtgcga agcaccaagc ctacgccgtc tcgcgcaata atataccgcg gtgtcctcgg      240
cacgcaggct gttcatttgc agatacagcg tgttcttgga attgtcacgg gagatggtga      300
accggccctt cacggagtct gcgtagtatg tgctaccgtt agtggcacca atggttgata      360
cccactctag acccttccct ggagcctggc ggacccaggc catagtctaa tcgttaaacc      420
tatatccgga ggctgcacag gagagacgca gggaccccc aggctgtacc aagcctcccc       480
cagactccaa cagctgcacc tgggccatgg ccggctgggc gcatagaaa ggtaccacta       540 aaggaatttg cgaataataa ttttttcatt atgactgtct ccttgaaata gaatttgcat      600
gcaagcttgg cgtaatcatg gtcatagctg tttcctgtgt gaaattgtta tccgctcaca      660
attccacaca acatacgagc cggaagcata agtgtaaag cctggggtgc ctaatgagtg       720
agctaactca cattaattgc gttgcgctca ctgcccgctt ccagtcggg aaacctgtcg       780 tgccagctgc attaatgaat cggccaacgc gcggggagag gcggtttgcg tattgggcgc      840
tcttccgctt cctcgctcac tgactcgctg cgctccgg                             878
```

<210> SEQ ID NO 11
<211> LENGTH: 905
<212> TYPE: DNA
<213> ORGANISM: Artificial Sequence
<220> FEATURE:
<223> OTHER INFORMATION: Recombinant polynucleotide

<400> SEQUENCE: 11

```
gttagtaaat gaattttctg tatgaggttt tgctaaacaa ctttcacagt ctatgcggcc       60 cccttttccaa gtcggttcat ctctatgtct gtataatgtg cggccgaatt cagatcctct     120
tctgagatga gtttttgttc tgcggccgcg ctcgagacgg tgaccagggt tccctgaccc     180
caagagtaga agttggtcgg ccgctgcctc gcctatctcg cgcaataata taccgcggtg     240
```

```
tcctcggcac gcaggctgtt catttgcaga tacagcgtgt tcttggaatt gtcacgggag      300
atggtgaacc ggcccttcac ggagtctgcg tagtatgtgc taccgtcacg gttcctaatg      360 gttgatacce actctagacc cttccctgga gcctggcgga cccagctcat atagtgagag      420
ttaaacttat atccggaggc tgcacaggag agacgcaggg accccccagg ctgtaccaag      480
cctcccccag actccaacag ctgcacctgg gccatggccg gctgggccgc ctagaaaggt      540
accactaaag gaattgcgaa taataatttt tttcattatg actgtctcct tgaaatagaa      600
tttgcatgca agcttggcgt aatcatggtc atagctgttt cctgtgtgaa attgttatcc      660
gctcacaatt ccacacaac atacgagccg gaaagcataa agtgtaaagc ctggggggtgc      720 ctaatgagtg agctaactca cattaattgc gttgcgctca ctgcccgctt tccagtcgg      780 ggaaacctgt cgtgccagct gcattaatga atcggcccaa cgcgcgggga gaggcggttt      840
tgcgtattgg gcgctcttcc gcttcctcg cctcactgac ttcgctgcgc tcgggtcgtt      900
cggct                                                                 905

<210> SEQ ID NO 12
<211> LENGTH: 673
<212> TYPE: DNA
<213> ORGANISM: Artificial Sequence
<220> FEATURE:
<223> OTHER INFORMATION: Recombinant polynucleotide

<400> SEQUENCE: 12
aaatgaattt tctgtatgag gtttccgcta acaactttc aacagtctat gcggccccct       60
ttccaagtcg gttcatctct atgtctgtat aatgtgcggc cgaattcaga tcctcttctg     120
agatgagttt ttgttctgcg gccgcgctcg agacggtgac cagggttccc tgaccccaag     180
actcgaccta gttgggagtc gccaacctcc acctattaac tctcgcgcaa taatataccg     240
cggtgtcctc ggcacgcagg ctgttcattt gcagatacag cgtgttcttg gaattgtcac     300
gggagatggt gaaccggccc ttcacggagt ctgcgtagta tgtgctaccg tcacgggtct     360
taatggttga tacccactct agacccttcc ctggagcctg gcggacccag cccatatact     420
tagggataac cctaaatcct gaggctgcac aggagagacg caggacccc ccaggctgta     480 ccaagcctcc cccagactcc aacagctgca cctgggccat ggccggctgg gccgcataga     540
aaggtaccac taaggaatt gcgaataata attttttcca ttatgactgt ctccttgaaa     600
tagaattttg catgcaagct ggcgtaatc atggtcatag ctgtttcctg tgtgaaattg     660
ttatcccgct cac                                                        673

<210> SEQ ID NO 13
<211> LENGTH: 957
<212> TYPE: DNA
<213> ORGANISM: Artificial Sequence
<220> FEATURE:
<223> OTHER INFORMATION: Recombinant polynucleotide

<400> SEQUENCE: 13
agttagtaaa tgaatttct gtatgaggtt ttgctaaaca actttcaaca gtctatgcgg       60
ccccctttca gtcggttca tctctatgtc tgtataatgt gcggccgaat tcagatcctc     120
ttctgagatg agtttttgtt ctgcggccgc gctcgagacg tgaccaggg ttccctgacc     180 ccaaaagcgc atgtgcggct tcctcatcat acccggaaac ctccccatcc ccttctttct     240
cgcgcaataa tataccgcgg tgtcctcggc acgcaggctg ttcatttgca gatacagcgt     300
gttcttggaa ttgtcacggg agatggtgaa ccggcccttc acggagtctg cgtagtatgt     360
```

```
gctaccgctt ggggcacgaa tggctgatac ccactctaga cccttccctg gagcctggcg        420
gacccagctc atatcctaat tgttaagcat aaatccggag gctgcacagg agagacgcag        480
ggacccccca ggctgtacca agcctccccc agactccaac agctgcacct gggccatggc        540
cggctgggcc gcatagaaag gtaccactaa aggaattgcg aataataatt ttttcattat        600
gactgtctcc ttgaaataga atttgcatgc aagcttggcg taatcatggt catagctgtt        660
tcctgtgtga aattgttatc cgctcacaat tccacacaac atacgagccg aagcataaa        720 gtgtaaagcc tggggtgcct aatgagtgag ctaactcaca ttaattgcgt tgcgctcact        780
gcccgctttc cagtcgggaa acctgtcgtg ccagctgcat taatgaatcg ccaacgcgc        840 ggggagaggc ggtttgcgta ttgggcgctc ttccgcttcc tcgctcactg actccgctgc        900
gctcggtcgt tcggctgcgg cgagcggtat cagctcactc aaaggcggta atacggt        957

<210> SEQ ID NO 14
<211> LENGTH: 374
<212> TYPE: DNA
<213> ORGANISM: Artificial Sequence
<220> FEATURE:
<223> OTHER INFORMATION: Recombinant polynucleotide

<400> SEQUENCE: 14
aacagtctat gcggcccccct ttccaagccc ggttcatctc tatgtctgta taatgtgcgg         60
ccgaattcag atcctcttct gagatgagtt tttgttctgc ggccgcgctc gagacggtga        120
ccagggttcc ctgaccccaa tacctcatcg acttgtgctg ctaatccccc ccccgatacc        180
gacaacgcct cctcccacaa ctcgcgcaat aatataccgc ggtgtcctcg gcccgcaggc        240
tgttcatttg cagatacagc gtgttcttgg aattgtcacg ggagatggtg aaccggccct        300
tcacggagtc tgcgtagtat gtgctaccgt tacggttccg aatgcttgat acccactcta        360 gaccccttccc tgga                                                         374

<210> SEQ ID NO 15
<211> LENGTH: 731
<212> TYPE: DNA
<213> ORGANISM: Artificial Sequence
<220> FEATURE:
<223> OTHER INFORMATION: Recombinant polynucleotide

<400> SEQUENCE: 15
cggttcatct ctatgtctgt ataatgtgcg gccgaattca gatcctcttc tgagatgagt         60
ttttgttctg cggccgcgct cgagacggtg accagggttc cctgacccca aaaccgcaag        120
ttctcggccc gcaccacatt accccgccac gccatcggtc tcgcgcaata atataccgcg        180
gtgtcctcgg cacgcaggct gttcatttgc agatacagcg tgtgcttgga attgtcacgg        240
gagatggtga accggccctt cacggagtct gcgtagtatg tgctaccgtt attcatctta        300
atggttgata cccactctag acccttccct ggagcctggc ggacccagct catatactaa        360
gcgctaaact aaatccgga ggctgcacag gagagacgca gggaccccccc aggctgtacc        420 aagcctcccc cagactccaa cagctgcacc tgggccatgg ccggctgggc cgcatagaaa        480
ggtaccacta aaggaattgc gaataataat ttttcatta tgactgtctc cttgaaatag        540
aattttgcat gcaagcttgg cgtaatcatg gtcatagctg ttttcctgtg tgaaattgtt        600
atccgctcac aattccacac aacatacgag ccggaagcat aaagtgtaaa gcctgggggt        660
gcctaaatga gtgagctaac tcacattaat tgcgttgcgc tcactgcccg ctttccagtc        720
```

```
gggaaacctg t                                                              731
```

<210> SEQ ID NO 16
<211> LENGTH: 439
<212> TYPE: DNA
<213> ORGANISM: Artificial Sequence
<220> FEATURE:
<223> OTHER INFORMATION: Recombinant polynucleotide

<400> SEQUENCE: 16

```
gttagtaaat gaattttctg tatgaggttt tgctaaacaa ctttcacagt ctatgcggcc          60
cccttccag tcggttcatc tctatgtctg tataatgtgc ggccgaattc agatcctctt         120
ctgagatgag ttttttgttct gcggccgcgc tcgagacggt gaccagggtt ccctgacccc        180
aaaacttgaa cttgtccggc aacgacaacc gcctctaact cgcgcaataa tataccgcgg        240
cgtcctcggc acgcatgctg ttcatataca gatacatcgt gttcttggaa ttgtcacggg        300
agatggggaa ccggcccttc acggagtctg cgtagtatgt gctaccgcta cgcatcccaa        360
tgcttgatac ccaatctaga cccttccctg agcctggcg acccaggcc atattctaat          420
ggctaatctt aactgctga                                                     439
```

<210> SEQ ID NO 17
<211> LENGTH: 716
<212> TYPE: DNA
<213> ORGANISM: Artificial Sequence
<220> FEATURE:
<223> OTHER INFORMATION: Recombinant polynucleotide

<400> SEQUENCE: 17

```
acagtctatg cggccccctt ccaagtcgg ttcatctcta tgtctgtata atgtgcggcc          60
gaattcagat cctcttctga gatgagtttt tgttctgcgg ccgcgctcga cggtgacc          120
agggttccct gaccccaaaa ctggaccgtg gtcggacaca ataccaccg acctctcgcg        180
caatgatata ccgcggtgtc ctcggcacgc aggctgttca tttgcagata cagcgtgttc        240
ttggaattgt cacgggagat ggtgaaccgg cccttcacgg agtctgcgta gtatgtgcta        300
ccgctacgga taccaatgct tgatacccac tctagaccct ccctggagc ctggcggacc        360
cagcccatat tctaatggct aagcttaact ccggaggctg cacaggagag acgcagggac        420
cccccaggct gtaccaagcc tcccccagac tccaacagct gcacctgggc catggccggc        480
tgggccgcat agaaaggtac cactaaagga attgcgaata taattttttt cattatgact        540
gtctccttga atagaatttt gcatgcaagc ttggcgtaat catggtcata gctgtttcct        600
gtgtgaaatt gttatccgct cacaattcca cacaaacata cgagccggaa gcataaagtg        660
taaagccctg gggtgcctaa tgagtgagct aactcacatt aattgcgttg cgctca           716
```

<210> SEQ ID NO 18
<211> LENGTH: 802
<212> TYPE: DNA
<213> ORGANISM: Artificial Sequence
<220> FEATURE:
<223> OTHER INFORMATION: Recombinant polynucleotide

<400> SEQUENCE: 18

```
tctgtatgag gttttgctaa caactttca acagtctatg cggccccctt ccaagtcgg          60
ttcatctcta tgtctgtata atgtgcggcc gaattcagat cctcttctga gatgagtttt       120
tgttctgcgg ccgcgctcga cggtgacc agggttccct gaccccaaaa cttgaacttg        180
ttcggaaacg acaaccgcct ctaactcgcg caataatata ccgcggtgtc ctcggcacgc        240
```

```
aggctgttca tttgcagata cagcgtgttc ttggaattgt cacgggagat ggtgaaccgg    300
cccttcacgg agtctgcgta gtatgtgcta ccgctacgca tcccaatgct tgatacccac    360
tctagaccct tccctggagc ctggcggacc caggccatat tctaacggct aatcttaact    420
ccggaggctg cacaggagag acgaagggac cccccaggct gtaccaagcc tcccccagac    480
tccaacagct gcacctgggc catggccggc tgggccgcat agaaaggtac cactaaagga    540
attgcgaata taattttttt cattatgact gtctccttga aatagaattt gcatgcaagc    600
ttggcgtaat catggtcata gctgtttcct gtgtgaaatt gttatccgct cacaattcca    660
cacaacatac gagcccggaa gcataaagcg taaagccctg ggggtgccct aaatgagcga    720
gctaactcac attaatcgcg ttggcgctca ctgcccgctt tccagtcggc aaaacctgcg    780
tgccagctgc attaatgaat cg                                              802
```

<210> SEQ ID NO 19
<211> LENGTH: 643
<212> TYPE: DNA
<213> ORGANISM: Artificial Sequence
<220> FEATURE:
<223> OTHER INFORMATION: Recombinant polynucleotide

<400> SEQUENCE: 19

```
aacaacctttt caacagtcta tgcggccccc tttccaagtc ggttcatctc tatgtctgta     60
taatgtgcgg ccgaattcag atcctcttct gagatgagtt tttgttctgc ggccgcgctc    120
gagacggtga ccagggttcc ctgacccaa gacttgaagg cgtggtgcct accccaacgc     180
cgatcaacac cactcgcgca ataatatacc gcggtgtcct cggcacgcag gctgttcatt    240
tgcagataca gcgtgttctt ggaattgtca cgggagatgg tgaaccggcc cttcacggag    300
tctgcgtagt atgtgctacc gttacgcgtc gcaatgcttg atacccactc tagacccttc    360
cctggagcct ggcggaccca gctcatagtc ttagggttaa gcctaactca ggaggctgca    420
caggaaagac gcagggaccc cccaggctgt accaagcctc ccccagactc aacagctgc    480 acctgggcca tggccggctg ggccgcatag aaaggcacaa ctaaaggaat tgcgaataat    540
aattttttca ttatgactgt ctccttgaaa tagaatttgc atgccagctt ggcgtaacca    600
tggtcatagc tgttttcctg tgtgaaattg ttatccgctc aca                      643
```

<210> SEQ ID NO 20
<211> LENGTH: 841
<212> TYPE: DNA
<213> ORGANISM: Artificial Sequence
<220> FEATURE:
<223> OTHER INFORMATION: Recombinant polynucleotide

<400> SEQUENCE: 20

```
gttagtaaat gaattttctg tatgaggttt cgctaaacaa ctttcacagt ctatgcggcc     60
ccctttccaa gtcggttcat ctctatgtct gtataatgtg cggccgaatt cagatcctct    120
tctgagatga gttttgttc tgcggccgcg ctcgagacgg tgaccagggt tccctgaccc    180
caagaccaca aggaggacgt ctgaccctcc tcactattcc gccgcccctt ccgtctcgcg    240
caataatata ccgcggtgtc ctcggcacgc aggctgttca tttgcagata cagcgtgttc    300
ttggaattgt cacgggagat ggtgaaccgg cccttcacgg agtctgcgta gtatgtgcta    360
ccgtcacgct tacgaatggt tgatacccac tctagaccct tccctggagc ctggcggacc    420
cagcccatat actaatagtt aaagctatat ccggaggctg cacaggagag acgcagggac    480
```

```
cccccaggct gtaccaagcc tcccccagac tccaacagct gcacctgggc catggccggc    540
tgggccgcat agaaaggtac cactaaagga attgcgaata ataattttt cattatgact    600 gtctccttga aatagaattt gcatgcaagc ttggcgtaat catggtcata gctgtttcct    660
gtgtgaaatt gttatccgct cacaattcca cacaacatac gagccggaag cataaagtgt    720
aaagcctggg gtgcctactg agtgagctaa ctcacattaa ttgcgttgcg ctcactgccc    780
gctttccagt cggaaaccct gtcgtgccag ctgcattaat gaatcggcca acgcgcgggg    840
a                                                                   841
```

<210> SEQ ID NO 21
<211> LENGTH: 608
<212> TYPE: DNA
<213> ORGANISM: Artificial Sequence
<220> FEATURE:
<223> OTHER INFORMATION: Recombinant polynucleotide

<400> SEQUENCE: 21

```
aacaactttc aacagtctat gcggcccct ttcaagtcgg ttcatctcta tgtctgtata     60
atgtgcggcc gaattcagat cctcttctga gatgagtttt tgttctgcgg ccgcgctcga   120
gacggtgacc agggttccct gaccccaaaa cttgaacttg ttcggaaacg acaaccgcct   180
ctaactcgcg caataatata ccgcggtgtc ctcggcacgc aggctgttca tttgcagata   240
cagcgtgttc ttggaattgt cacgggagat ggtgaaccgg cccttcacgg agtctgcgta   300
gtatgtgcta ccgctacgca tcccaatgct tgataccac tctagaccct ccctggagc    360 ctggcgacc caggccatat tctaatggct aatcttaact ccggaggctg cacaggagag    420
acgaagggac cccccaggct gtaccaagcc tcccccagac tccaacagct gcacctgggc    480
catggccggc tgggccgcat agaaaggtac cactaaagga attgcgaata ataatttttt   540
cattatgact gtctccttga aatagaattt gcatgcaagc ttggccgtaa tcatggtcat    600
agctgttt                                                           608
```

<210> SEQ ID NO 22
<211> LENGTH: 747
<212> TYPE: DNA
<213> ORGANISM: Artificial Sequence
<220> FEATURE:
<223> OTHER INFORMATION: Recombinant polynucleotide

<400> SEQUENCE: 22

```
tagtaaatga attttctgta tgaggttttg ctaaacaact ttcaacagtc tatgcggccc     60
cctttccagt cggttcatct ctatgtctgt ataatgtgcg gccgaattca gatcctcttc   120
tgagatgagt ttttgttctg cggccgcgct cgagacggtg accagggttc ctgaccccca   180
aaactggacg gtcgtcggac gcatatacta ccgacctctc gcgcaatgat ataccgcggt   240
gtcctcggca cgcaggctgt tcatttgcag atacagcgtg ttcttggaat tgtcacggga   300
gatggtgaac cggcccttca cggagtctgc gtagtatgtg ctaccgtcac ggccacgaat   360
gcttgatacc cactctagac ccttccctgg agcctggcgg acccagccca tattcttatg   420
ggtaagccta actccggagg ctgcacagga gagacgcagg gaccccccag gctgtaccaa   480
gcctccccca gactccaaca gctgcacctg gccatggcc ggctggtccg catagaaagg    540
taccactaaa ggaattgcga ataataattt tttcattatg actgtctcct tgaaatagaa   600
tttgcatgcc ggcttggcgt aatcatggtc atagctgttt cctgtgtgaa attgttatcc   660
gctcacaatt ccacacaaca tactagccgg aagcataaag tgtaaagcct ggggtgccta   720
```

```
atgagtgagc taactcacat taattgc                                          747
```

<210> SEQ ID NO 23
<211> LENGTH: 696
<212> TYPE: DNA
<213> ORGANISM: Artificial Sequence
<220> FEATURE:
<223> OTHER INFORMATION: Recombinant polynucleotide

<400> SEQUENCE: 23

```
aacagtctat gcggccccct ttccagtcgg ttcatctcta tgtctgtata atgtgcggcc      60
gaattcagat cctcttctga gatgagtttt tgttctgcgg ccgcgctcga cggtgacc       120
agggttccct gaccccaaaa cttgatgtac ttcgtacgaa aaggcccccg acgcccactc    180
gcgcaataat ataccgcggt gtcctcggca cgcaggctgt tcatttgcag atacagcgtg    240
ttcttggaat tgtcacggga gatggtgaac cggcccttca cggagtctgc gtagtatgtg    300
ctaccgcttc ggctattaat gcctgatacc cactctagac ccttccctgg agcctggcgg   360
acccagctca taaactaatg gttaaaccta actccggagg ctgcacagga gagacgcagg   420
gaccccccag gctgtaccaa gcctccccca gactccaaca gctgcacctg gccatggcc    480
ggctgggccg catagaaagg taccactaaa ggaattgcga ataataattt tttcattatg   540
actgtctcct tgaaatagaa tttgcatgca agcttggccg taatcatggt catagctgtt   600
tcctgtgtga aattgttatc cgctcacaa ttccacacaa catacgagcc gggaagcata    660
aagtgtaaag cctgggggtg cctaatgagt gagcta                             696
```

<210> SEQ ID NO 24
<211> LENGTH: 920
<212> TYPE: DNA
<213> ORGANISM: Artificial Sequence
<220> FEATURE:
<223> OTHER INFORMATION: Recombinant polynucleotide

<400> SEQUENCE: 24

```
ttagtaaatg aattttctgt atgaggtttt gctaaacaac tttcaacagt ctatgcggcc     60
ccctttccag tcggttcatc tctatgtctg tataatgtgc ggccgaattc agatcctctt   120
ctgagatgag ttttttgttct gcggccgcgc tcgagacggt gaccagggtt ccctgacccc   180
aaaaccgcaa gttctcggcc cgcaccacat taccccgcca cgccatcggt ctcgcgcaat   240
aatataccgc ggtgtcctcg gcacgcaggc tgttcatttg cagatacagc gtgtgcttgg   300
aattgtcacg ggagatggtg aaccggcccct tcacggagtc tgcgtagtat gtgctaccgt   360
tattcatctt aatggttgat acccactcta gaccccttccc tggagcctgg cggacccagc   420
tcatatacta agcgctaaac ttaaatccgg aggctgcaca ggagagacgc agggaccccc   480
caggctgtac caagcctccc ccagactcca acagctgcac ctgggccatg gccggctggg   540
ccgcatagaa aggtaccact aaaggaattg cgaataataa tttttttcatt atgactgtct   600
ccttgaaata gaatttgcat gcaagcttgg cgtaatcatg gtcatagctg tttcctgtgt   660
gaaattgtta tccgctcaca attccacaca acatacgagc cggaagcata aagtgtaaag   720
cctgggggtgc ctaatgagtg agctaactca cattaattgc gttgcgctca cgcccgcttt   780
ccagtcggga aacctgtcgt gccagctgca ttaatgaatc ggccaacgcg cggggagagg   840
cggtttgcgt attgggcgct cttccgcttc ctcgctcact gactcgctgc gctcggtcgt   900
tcggctgctg cgagcggtat                                               920
```

<210> SEQ ID NO 25
<211> LENGTH: 884
<212> TYPE: DNA
<213> ORGANISM: Artificial Sequence
<220> FEATURE:
<223> OTHER INFORMATION: Recombinant polynucleotide

<400> SEQUENCE: 25

| | | | | | |
|---|---|---|---|---|---|
| ttagtaaatg | aattttctgt | atgaggtttt | gctaaacaac | tttcaacagt | ctatgcggcc | 60 |
| cccttttcaag | tcggttcatc | tctatgtctg | tataatgtgc | ggccgaattc | agatcctctt | 120 |
| ctgagatgag | tttttgttct | gcggccgcgc | tcgagacggt | gaccagggtt | ccctgacccc | 180 |
| aaaacttgaa | cttgttcgga | aactacaacc | gcctctaact | cgcgcaataa | tataccgcgg | 240 |
| tgtcctcggc | acgcaggctg | ttcatttgca | gatacagcgt | gttcttggaa | ttgtcacggg | 300 |
| agatggtgaa | ccggcccttc | acggagtctg | cgtagtatgt | gctaccgcta | cgcatcccaa | 360 |
| tgcttgatac | ccactctaga | cccttccctg | gagcctggcg | gacccaggcc | atattctaat | 420 |
| ggctaatctt | aactccggag | gctgcacagg | agagacgaag | gaccccccca | ggctgtacca | 480 |
| agcctccccc | agactccaac | agctgcacct | gggccatggc | cggctgggcc | gcatagaaag | 540 |
| gtaccactaa | aggaattgcg | aataataatt | ttttcattat | gactgtctcc | ttgaaataga | 600 |
| atttgcatgc | aagcttggcg | taatcatggt | catagctgtt | cctgtgtga | aattgttatc | 660 |
| cgctcacaat | tccacacaac | atacgagccg | gaagcataaa | gtgtaaagcc | tggggtgcct | 720 |
| aatgagtgag | ctaactcaca | ttaattgcgt | tgcgctcact | gcccgctttc | cagtcgggaa | 780 |
| acctgtcgtg | ccagctgcat | taatgaatcg | gccaacgcgc | gggagaggcg | gcttgcgta | 840 |
| ttgggcgctc | ttccgcttcc | tcgctcactg | actcgctgcg | ctcg | | 884 |

<210> SEQ ID NO 26
<211> LENGTH: 835
<212> TYPE: DNA
<213> ORGANISM: Artificial Sequence
<220> FEATURE:
<223> OTHER INFORMATION: Recombinant polynucleotide

<400> SEQUENCE: 26

| | | | | | |
|---|---|---|---|---|---|
| tagtaaatga | attttctgta | tgaggttttg | ctaaacaact | ttcaacagtc | tatgcggccc | 60 |
| cctttccaag | tcggttcatc | tctatgtctg | tataatgtgc | ggccgaattc | agatcctctt | 120 |
| ctgagatgag | tttttgttct | gcggccgcgc | tcgagacggt | gaccagggtt | ccctgacccc | 180 |
| aataccggaa | cgtgttgtta | acccaagccc | gctttgtcgc | gcaataatat | accgcggtgt | 240 |
| cctcggcacg | caggctgttc | atttgcagat | acagcgtgtt | cttggaattg | tcacgggaga | 300 |
| tggtgaaccg | gcccttcacg | gagtctgcgt | agtatgtgct | accgttttg | ttctgaatgg | 360 |
| ttgataccca | ctctagaccc | ttccctggag | cctggcggac | ccagctcata | gccttatagc | 420 |
| taaccctaac | tccggaggct | gcacaggaga | gacgcaggga | cccccaggc | tgtaccaagc | 480 |
| ctccccccaga | ctccaacagc | tgcacctggg | ccatggccgg | ctaggccgca | tagaaaggta | 540 |
| ccactaaagg | aattgcgaat | aataattttt | tcattatgac | tgtctccttg | aaatagaatt | 600 |
| tgcatgcaag | cttggcgtaa | tcatggtcat | agctgttttcc | tgtgtgaaat | tgttatccgc | 660 |
| tcacaattcc | acacaacata | cgagccggaa | gcataaagtg | taaagcctgg | ggtgcctaat | 720 |
| gagtgagcta | actcacattt | aattgcgttg | cgctcactgc | ccgctttcca | gtcgggaaac | 780 |
| ctgtcgtgcc | agctgcatta | atgaatcggc | caacgcgcgg | ggagaggcgg | tttgc | 835 |

<210> SEQ ID NO 27
<211> LENGTH: 978
<212> TYPE: DNA
<213> ORGANISM: Artificial Sequence
<220> FEATURE:
<223> OTHER INFORMATION: Recombinant polynucleotide

<400> SEQUENCE: 27

```
tagtaaatga attttctgta tgaggttttg ctaaacaact ttcacagtct atgcggcccc      60
ctttccagtc ggttcatctc tatgtctgta aatgtgcggc cgaattcag atcctcttct     120
gagatgagtt tttgttctgc ggccgcgctc gagacggtga ccagggttcc ctgaccccaa    180
gaccacaagg aggacgtctg accctcctca ctattccgcc gccccttccg tctcgcgcaa    240
taatataccg cggtgtcctc ggcacgcagg ctgttcattt gcagatacag cgtgttcttg    300
gaattgtcac gggagatggt gaaccggccc ttcacggagt ctgcgtagta tgtgctaccg    360
tcacgcttac gaatggttga tacccactct agacccttcc ctggagcctg cggacccag    420
cccatatact aatagttaaa gctatatccg gaggctgcac aggagagacg cagggacccc    480
ccaggctgta ccaagcctcc cccagactcc aacagctgca cctgggccat ggccggctgg    540
gccgcataga aaggtaccac taaggaatt gcgaataata atttttttcat tatgactgtc    600
tccttgaaat agaatttgca tgcaagcttg gcgtaatcat ggtcatagct gtttcctgtg    660
tgaaattgtt atccgctcac aattccacac aacatacgag ccggaagcat aaagtgtaaa    720
gcctggggtg cctaatgagt gagctaactc acattaattg cgttgcgctc actgcccgct    780
ttccagtcgg gaaacctgtc gtgccagctg cattaatgaa tcggccaacg cgcggggag    840
aggcggtttg cgtattgggc gctcttccgc ttccttcgct cactgactcg ctgcgctcgg    900
tcgttcggct gcgggcgagc ggtatcagct cactcaaagg cggtaatacg gttatccaca    960
gaatcagggg ataacgca                                                  978
```

<210> SEQ ID NO 28
<211> LENGTH: 841
<212> TYPE: DNA
<213> ORGANISM: Artificial Sequence
<220> FEATURE:
<223> OTHER INFORMATION: Recombinant polynucleotide

<400> SEQUENCE: 28

```
aaatgaattt tctgtatgag gtttccgcta acaactttc aacagtctat gcggccccct      60
ttccaagtcg gttcatctct atgtctgtat aatgtgcggc cgaattcaga tcctcttctg    120
agatgagttt ttgttctgcg gccgcgctcg agacggtgac cagggttccc tgaccccaag    180
accgcaactc ggacttaata ttattcaact cattccgatg acgaaccctca ctcgcgcaat    240
aatataccgc ggtgtcctcg gcacgcaggc tgttcatttg cagatacagc gtgttcttgg    300
aattgtcacg ggagatggtg aaccggccct tcacggagtc tgcgtagtat gtgctaccgt    360
catggctacg aatgcttgat acccactcta gacccttccc tggagcctgg cggacccagg    420
ccatattcta agagataacc ttaaatccgg aggctgcaca ggagagacgc agggaccccc    480
caggctgtac caagcctccc ccagactcca acagctgcac ctgggccatg gccggctggg    540
ccgcatagaa aggtaccact aaaggaattg cgaataataa ttttttcatt atgactgtct    600
ccttgaaata gaatttgcat gcaagcttgg cgtaatcatg gtcatagctg tttcctgtgt    660
gaaattgtta tccgctcaca aatttccaca acgtacga gccggaagca taaagtgtaa    720
agcctggggt gcctaatgag tgagctaact cacattaatt gcgtttgcgc tcactgcccg    780
```

```
atttccagtc gggaaacctg tcgtgccagc tgcattaatg aatcggccaa cgcgcgggga    840
g                                                                    841

<210> SEQ ID NO 29
<211> LENGTH: 568
<212> TYPE: DNA
<213> ORGANISM: Artificial Sequence
<220> FEATURE:
<223> OTHER INFORMATION: Recombinant polynucleotide

<400> SEQUENCE: 29
taaacaactt tcaacagtct atgcggcccc ctttcccgtc ggtttatctc tatgtctgta     60
taatgtgcgg ccgaattcag atcctcttct gagatgagtt tttgttctgc ggccgcgctc    120
gagacggtga ccagggttcc ctgaccccaa agtacatgg tggggttctt cacccacggc     180
caccgccttc tcgcgcaata atataccgcg gtgtcctcgg cacgcaggct gttcatttgc    240
agatacagcg tgttcttgga attgtcacgg gagatggtga accggccctt cacggagtct    300
gcgtagtatg tgctaccgtt tttcgtctga atggttgata cccactctag acccttccct    360
ggagcctggc ggacccaggc cataaactaa ttggtaaact taactccgga ggctgcacag    420
gagagacgca gggaccccc aggctgtacc aagcctcccc cagactccaa cagctgcacc    480
tgggccatgg ccggctgggc cgcatagaaa ggtaccacta aggaattgc gaataataat    540
tttttttcatt atgactgtct ccttgaaa                                      568

<210> SEQ ID NO 30
<211> LENGTH: 860
<212> TYPE: DNA
<213> ORGANISM: Artificial Sequence
<220> FEATURE:
<223> OTHER INFORMATION: Recombinant polynucleotide

<400> SEQUENCE: 30
gttagtaaat gaattttctg tatgaggttt tcgctaaaca actttcaaca gtctatgcgg     60
ccccctttcc aagtcggttc atctctatgt ctgtataatg tgcggccgaa ttcagatcct    120
cttctgagat gagttttgt tctgcggccg cgctcgagac ggtgaccagg gttccctgac    180
cccaatacga cagcttctcc gtacgcccct tacgtctcgc gcaataatat accgcggtgt    240
cctcggcacg caggctgttc atttgcagat acagcgtgtt cttggaattg tcacgggaga    300
tggtgaaccg gcccttcacg gagtctgcgt agtatgtgct accgtctttc ccctaaatgg    360
ctgatacccca ctctagaccc ttccctggag cctggcggac ccaggccata ttgttatagc    420
taaacgtaaa tccggaggct gcacaggaga gacgcaggga cccccaggc tgtaccaagc    480
ctcccccaga ctccaacagc tgcacctggg caatggccgg ctgggccgca tagaaaggta    540
ccactaaagg aattgcgaat aataattttt tcattatgac tgtctccttg aaatagaatt    600
tgcatgcaag cttggcgtaa tcatggtcat agctgtttcc tgtgtgaaat tgttatccgc    660
tcacaattcc acacaacata cgagccggac agcataaagt gtaaagccc tggggtgcct    720
aacgagtgag ctaactcaca ttaattgcgt tgcgctcact gcccgctttt ccagtcgggg    780
aaacccgtcg tgcccagctg cattaatgaa tcggccaac gcgcgggag aggcggttt    840
gcgtattgcg ccgctcttcc                                                860

<210> SEQ ID NO 31
<211> LENGTH: 774
<212> TYPE: DNA
<213> ORGANISM: Artificial Sequence
```

<220> FEATURE:
<223> OTHER INFORMATION: Recombinant polynucleotide

<400> SEQUENCE: 31

```
ttagtaaatg aattttctgt atgaggtttt gctaaacaac tttcaacagt ctatgcggcc      60
cccctttcaag tcggttcatc tctatgtctg tataatgtgc ggccgaattc agatcctctt    120
ctgagatgag tttttgttct gcggccgcgc tcgagacggt gaccagggtt ccctgacccc     180
aagacctcat cttggcggtc ccatgcaaac ccaaacgccc tctcgcgcaa taataccg       240
cggtgtcctc ggcacgcagg ctgttcattt gcagatacag cgtgttcttg gaattgtcac     300
gggagatggt gaaccggccc ttcacggagt ctgcgtagta tgtgctaccg tctgtcgcac     360
caatggctga tacccactct agaccttcc ctggagcctg gcggacccag cccatagcct      420
aagggttaaa cttaactccg gaggctgcac aggagagacg cagggacccc ccaggctgta     480
ccaagcctcc cccagactcc aacagctgca cctgggccat ggccggctgg gccgcataga    540
aaggtaccac taaggaatt gcaataata attttttcat tatgactgtc tccttgaaat       600
agaatttgca tgcaagcttg gcgtaatcat ggtcatagct gtttcctgtg tgaaattgtt     660
atccgctcac aattccacac aacatacgag ccggaagcat aaagtgtaaa gcgctggggt     720
gcctaatgag tgagctaact cacattaatt gcgttgcgct cactgcgccg cttt           774
```

<210> SEQ ID NO 32
<211> LENGTH: 757
<212> TYPE: DNA
<213> ORGANISM: Artificial Sequence
<220> FEATURE:
<223> OTHER INFORMATION: Recombinant polynucleotide

<400> SEQUENCE: 32

```
taaacaactt tcaacagtct atgcggcccc ctttccagtc ggttcatctc tatgtctgta     60
taatgtgcgg ccgaattcag atcctcttct gagatgagtt tttgttctgc ggccgcgctc    120
gagacggtga ccagggttcc ctgaccccaa gaccgcacct aggcgggctt cctacgcccc    180
aaccgtgtcg cgcaataata taccgcggtg tcctcggcac gcaggctgtt catttgcaga    240
tacagcgtgt tcttggaatt gtcacgggag atggtgaacc ggcccttcac ggagtctgcg    300
tagtatgtgc taccgtttct gccaagaatg gttgatacc actctagacc cttccctgga    360
gcctggcgga cccaggtcat aacctaattg gtaacgttaa ctccggaggc tgcacaggag    420
agacgcaggg accccccagg ctgtaccaag cctcccccag actccaacag ctgcacctgg    480
gccatggccg gctgggccgc atagaaaggt accactaaag gaattgcgaa taataatttt    540
ttcattatga ctgtctcctt gaaatagaat ttgcatgcaa gcttggcgta atcatggtca    600
tagctgtttc ctgtgtgaaa ttgttatccg ctcacaattc cacacaacat acgagccgga    660
agcataaagt gtaaaagcct ggggtgccta atgagtgagc taactcacat taattgcgtt    720
gcgctcact gcccgctttc cagtcgggga aacctgt                              757
```

<210> SEQ ID NO 33
<211> LENGTH: 805
<212> TYPE: DNA
<213> ORGANISM: Artificial Sequence
<220> FEATURE:
<223> OTHER INFORMATION: Recombinant polynucleotide

<400> SEQUENCE: 33

```
ctaaacaact ttcaacagtc tatgcggccc cctttccaag tcggttcatc tctatgtctg     60
```

```
tataatgtgc ggccgaattc agatcctctt ctgagatgag ttttttgttct gcggccgcgc    120 tcgagacggt gaccggggtt ccctgacccc aatagcggaa gttggcggta cgcctcctcc    180
tacccgcgca ataatatacc gcggtgtcct cggcacgcag gctgttcatt tgcagataca    240
gcgtgttctt ggaattgtca cgggagatgg tgaaccggcc cttcacggag tctgcgtagt    300
atgtgctacc gcttccgata gcaatggttg atacccactc tagacccttc cctggagcct    360
ggcggaccca gcccatatcc taagtgttaa acctatatcc ggaggctgca caggagagac    420
gcagggaccc cccaggctgt accaagcctc ccccagactc aacagctgc acctgggcca    480 tggccggctg ggccgcatag aaaggtacca ctaaaggaat tgcgaataat aattttttca    540
ttatgactgt ctccttgaaa tagaatttgc atgcaagctt ggcgtaatca tggtcatagc    600
tgtttcctgt gtaaaattgt tatccgctca caattccaca caacatacga gccgaagca     660 taaagtgtaa agcctgggt gcctaatgag tgagctaact cacattaatt tgcgttgcgc     720
tcactgtccg ctttccagtc ggaaacctgt cgtgccagct gcattaatga atcggccaac    780
gcgcggggag aggcggtttg cgtat                                          805
```

<210> SEQ ID NO 34
<211> LENGTH: 862
<212> TYPE: DNA
<213> ORGANISM: Artificial Sequence
<220> FEATURE:
<223> OTHER INFORMATION: Recombinant polynucleotide

<400> SEQUENCE: 34

```
tagtaaatga attttctgta tgaggttttg ctaaacaact ttcaacagtc tatgcggccc     60
cctttccaag tcggttcatt tctatgtctg tataatgtgc ggccgaattc agatcctctt    120
ctgagatgag ttttttgttct gcggccgcgc tcgagacggt gaccagggtt ccctgacccc   180
aatagcgcaa ctgctgggtt ctaagacgac gtgtcgcgca ataatatacc gcggtgtcct    240
cggcacgcag gctgttcatt tgcagataca gcgtgttctt ggaattgtca cgggagatgg    300
tgaaccggcc cttcacggag tctgcgtagt atgtgctacc gtctcgctta caatggttg     360 atacccactc tagacccttc cctggagcct ggcggaccca gcccataatc taagtgttaa    420
cgctatctcc ggaggctgca caggagagac gcagggaccc cccaggctgt accaagcctc    480
ccccagactc aacagctgc acctgggcca tggccggctg ggccgcatag aaaggtacca     540
ctaaaggaat tgcgaataat aattttttca ttatgactgt ctccttgaaa tagaatttgc    600
atgcaagctt ggcgtaatca tggtcatagc tgtttcctgt gtgaaattgt tatccgctca    660
caattccaca caacatacga gccgaagca taaagtgtaa agcctgggt gcctaatgag      720 tgagctaact cacattaatt gcgttgcgct cactgccccg ctttccagtc gggaaacctg    780
tcgtgccagc tgcattaatg aaatcggccc aacgcgcggg gagagggcgg tttgcgtatt    840
gggcgctctt ccgcttcctc gc                                             862
```

<210> SEQ ID NO 35
<211> LENGTH: 658
<212> TYPE: DNA
<213> ORGANISM: Artificial Sequence
<220> FEATURE:
<223> OTHER INFORMATION: Recombinant polynucleotide

<400> SEQUENCE: 35

```
ccggttcatc tctatgtctg tataatgtgc ggccgaattc agatcctctt ctgagatgag     60 ttttttgttct gcggccgcgc tcgagacggt gaccagggtt ccctgacccc aagactgcac   120
```

| | |
|---|---|
| cttctaggga cgacgcccag tactcgcgca ataatatacc gcggtgtcct cggcacgcag | 180 |
| gctgttcatt tgcagataca gcgtgttctt ggaattgtca cggagatgg tgaaccggcc | 240 |
| cttcacggag tctgcgtagt atgtgctacc gctatggtta gcaatggttg atacccactc | 300 |
| tagacccttc cctggagcct ggcgacccca gctcataacc taattgctaa cgttaactcc | 360 |
| ggaggctgca caggagagac gcagggaccc ccaggctgt accaagcctc ccccagactc | 420 |
| caacagctgc acctgggcca tggccggctg ggccgcatag aaaggtacca cctaaaggaa | 480 |
| ttgcgaataa taatttttc attatgactg cctccttgaa atacaatttg catgcaagct | 540 |
| tggcgtactc atggccatag ctgttttcct gtgtgaaatt gttatccgct cacaattcca | 600 |
| cacaacatac gagccggacg cataaagtgt aaagcctggg gtgccctaat gagtgagc | 658 |

<210> SEQ ID NO 36
<211> LENGTH: 788
<212> TYPE: DNA
<213> ORGANISM: Artificial Sequence
<220> FEATURE:
<223> OTHER INFORMATION: Recombinant polynucleotide

<400> SEQUENCE: 36

| | |
|---|---|
| ctaaacaact ttcaacagtc tatgcggccc cctttccagt cggttcatct ctatgtctgt | 60 |
| ataatgtgcg gccgaattca gatcctcttc tgagatgagt ttttgttctg cggccgcgct | 120 |
| cgagacggtg accagggttc cctgacccca agactggatc gactgcgtca cctaacgctt | 180 |
| attcccctcc cgatttcccg cgcaataata taccgcggtg tcctcggcac gcaggctgtt | 240 |
| catttgcaga tacagcgtgt tcttggaatt gtcacgggag atggtgaacc ggcccttcac | 300 |
| ggagtctgcg tagtatgtgc taccgtctct gttcaaaatg gttgataccc actctagacc | 360 |
| cttccctgga gcctggcgga cccaggtcat aacctaagcg ctaatgttaa ctccggaggc | 420 |
| tgcacaggag agacgcaggg acccccccagg ctgtaccaag cctcccccag actccaacag | 480 |
| ctgcacctgg gccatggccg gctgggccgc atagaaaggt accactaaag gaattgcgaa | 540 |
| taataatttt ttcattatga ctgtctcctt gaaatagaat ttgcatgcaa gcttggcgta | 600 |
| atcatggtca tgctgtttcc tgtgtgaaat tgttatccgc tcacaattcc acacaacata | 660 |
| cgagccggaa gcataaagtg taaagcctgg ggtgcctaat gagtgagcta actcacatta | 720 |
| attgcgttgc gctcactgcc cgcttttccag tcgggaaaac ctgtcgtgcc agctgcatta | 780 |
| atgaatcg | 788 |

<210> SEQ ID NO 37
<211> LENGTH: 788
<212> TYPE: DNA
<213> ORGANISM: Artificial Sequence
<220> FEATURE:
<223> OTHER INFORMATION: Recombinant polynucleotide

<400> SEQUENCE: 37

| | |
|---|---|
| tagtaaatga attttctgta tgaggttttg ctaaacaact ttcacagtct atgcggcccc | 60 |
| ctttccaagt cggttcatct ctatgtctgt ataatgtgcg gccgaattca gatcctcttc | 120 |
| tgagatgagt ttttgttctg cggccgcgct cgagacggtg accagggttc cctgacccca | 180 |
| agactgcacc ggcgtcgtcc tcttccgcga cgttctcgcg caataatata ccgcggtgtc | 240 |
| ctcggcacgc aggctgttca tttgcagata cagcgtgttc ttggaattgt cacgggagat | 300 |
| ggtgaaccgg cccttcacgg agtctgcgta gtatgtgcta ccgctattgg tctaaatgcc | 360 |

```
tgatacccac tctagaccct tccctggagc ctggcggacc cagctcatat acttagggat     420
aaggctatct ccggaggctg cacaggagag acgcagggac cccccaggct gtaccaagcc     480
tcccccagac tccaacagct gcacctgggc catggccggc tgggccgcat agaaaggtac     540
cactaaagga attgcgaata ataatttttt cattatgact gtctccttga aatagaattt     600
gcatgcaagc ttggcgtaat catggtcata gctgtttcct gtgtgaaatt gttatccgct     660
cacaattcca cacaacatac gagccggaaa gcataaagtg taaagcctgg ggtgcctaat     720
gagtgagcta actcacatta attgcgttgc gctcactgcc cgctttccag tcgggaaacc     780
tgtcgtgc                                                              788

<210> SEQ ID NO 38
<211> LENGTH: 865
<212> TYPE: DNA
<213> ORGANISM: Artificial Sequence
<220> FEATURE:
<223> OTHER INFORMATION: Recombinant polynucleotide

<400> SEQUENCE: 38
gttagtaaat gaattttctg tatgaggttc ccgctaaaca actttcaaca gtctatgcgg     60 cccccttttcc aagtcggttc atctctatgt ctgtataatg tgcggccgaa ttcagatcct    120
cttctgagat gagttttgt tctgcggccg cgctcgagac ggtgaccagg gttccctgac      180
cccaagactg catgggcttg gtcgtactac gcttcttccc ctcgcgcaa taatataccg      240 cggtgtcctc ggcacgcagg ctgttcattt gcagatacag cgtgttcttg gaattgtcac    300
gggagatggt gaaccggccc ttcacggagt ctgcgtagta tgtgctaccg cttctgctct    360
aaatggttga tacccactct agacccttcc ctggagcctg gcggacccag ctcatatact    420
tatggataaa cgtaaatccg gaggctgcac aggagagacg cagggacccc ccaggctgta    480
ccaagcctcc cccagactcc aacagctgca cctgggccat ggccggctgg ccgcataga    540 aaggtaccac taaggaatt gcgaataata attttttcat tatgactgtc tccttgaaat    600
agaatttgca tgcaagcttg gcgtaatcat ggtcatagct gtttcctgtg tgaaattgtt    660
atcccgctca caattccaca acatacga gcccggaagc ataaagtgta aagcctgggg    720
gtgcctaatg agtgagctaa ctcacattaa ttgcgttgcg ctcactgccc gctttccagt    780
cggaaacctg tcgtgccagc tgcattaatg aatcggccaa cgcggggag aggcggtttg     840 cgtattgggc gctcttccgc ttcct                                           865

<210> SEQ ID NO 39
<211> LENGTH: 743
<212> TYPE: DNA
<213> ORGANISM: Artificial Sequence
<220> FEATURE:
<223> OTHER INFORMATION: Recombinant polynucleotide

<400> SEQUENCE: 39
acagtctatg cggccccctt ccaagtcgg ttcatctcta tgtctgtata atgtgcggcc      60
gaattcagat cctcttctga gatgagtttt tgttctgcgg ccgcgctcga cggtgacc     120 agggttccct gaccccaata cgggaccgtc ttgtaatcac tattccgctt ccgcgcaa     180 taatataccg cggtgtcctc ggcacgcagg ctgttcattt gcagatacag cgtgttcttg    240
gaattgtcac gggagatggt gaaccggccc ttcacggagt ctgcgtagta tgtgctaccg    300
tctttgccca taatggttga tacccactct agacccttcc ctggagcctg gcggacccag    360
gtcataatct aatagttaac cgtatatccg gaggctgcac aggagagacg cagggacccc    420
```

```
ccaggctgta ccaagcctcc cccagactcc aacagctgca cctgggccat ggccggctgg    480
gccgcataga aagtaccac taaaggaatt gcgaataata attttttcat tatgactgtc     540
tccttgaaat agaatttgca tgcaagcttg gcgtaatcat ggtcatagct gtttcctgtg    600
tgaaatttgt tatccgctca caattccaca acataacg agccggaagc ataaagtgta      660
aagcctgggg tgcctaatga gtgagctaac ctcacattaa tttgcgttgc gcttcactgc    720
cccgctttcc agtccgggaa acc                                            743
```

<210> SEQ ID NO 40
<211> LENGTH: 787
<212> TYPE: DNA
<213> ORGANISM: Artificial Sequence
<220> FEATURE:
<223> OTHER INFORMATION: Recombinant polynucleotide

<400> SEQUENCE: 40

```
aatgaatttt ctgtatgagg ttttgctaaa caactttcaa cagtctatgc ggccccctt     60 ccagtcggtt catctctatg tctgtataat gtgcggccga attcagatcc tcttctgaga    120 tgagttttg ttctgcggcc gcgctcgaga cggtgaccag ggttccctga ccccaaaact    180
tcaaggggtg cgtcaaatca cccctcgacc tccttcccgc gcaataatat accgcggtgt    240
cctcggcacg caggctgttc atttgcagat acagcgtgtt cttggaattg tcacgggaga    300
tggtgaaccg gcccttcacg gagtctgcgt agtatgtgct accgtcatgg ccaccaatgg    360
ttgataccca ctctagaccc ttccctggag cctggcggac ccagctcata ttctaatggt    420
taaccataaa tccggaggct gcacaggaga gacgcaggga ccccccaggc tgtaccaagc    480
ctcccccaga ctccaacagc tgcacctggg ccatggccgg ctgggccgca tagaaaggta    540
ccactaaagg aattgcgaat aataattttt tcattatgac tgtctccttg aaatagaatt    600
tgcatgcaag cttggcgtaa tcatggtcat agctgtttcc tgtgtgaaat tgttatccgc    660
tcacaattcc acaccaacat acgagccgga agcataaagt gtaaagcctg gggtgccta    720 aatgagtgag ctaactcaca ttaattgcgt tgcgctcact gccgctttcc agtcgggaaa    780
cctgtcg                                                             787
```

<210> SEQ ID NO 41
<211> LENGTH: 765
<212> TYPE: DNA
<213> ORGANISM: Artificial Sequence
<220> FEATURE:
<223> OTHER INFORMATION: Recombinant polynucleotide

<400> SEQUENCE: 41

```
gctaaacaac tttcaacagt ctatgcggcc cccttccag tcggttcatc tctatgtctg     60
tataatgtgc ggccgaattc agatcctctt ctgagatgag ttttgttct gcggccgcgc    120 tcgagacggt gaccagggtt ccctgacccc aagacctcac cttcgtctgc ctagcccct    180 ccaacaacct cctaagtgtc gcgcaataat ataccgcggt gtcctcggca cgcaggctgt    240
tcatttgcag atacagcgtg ttcttggaat tgtcacggga gatggtgaac cggcccttca    300
cggagtctgc gtagtatgtg ctaccgtctg ggttcctaat tgttgatacc cactctagac    360
ccttccctgg agcctggcgg acccaggcca tagtctaatt gctaaaccta tatccggagg    420
ctgcacagga gagacgcagg gaccccccag gctgtaccaa gctcccccca gactccaaca    480
gctgcacctg ggccatggcc ggctgggccg catagaaagg taccactaaa ggaattgcga    540
```

```
ataataattt tttcattatg actgtctcct tgaaatagaa tttgcatgca agcttggcgt    600
aatcatggtc atagctgttt cctgtgtgaa attgttatcc gctcacaatt ccacacaaca    660
tacgagccgg aagcataaag tgtaagcctg gggtgcctaa tgagtgagct aactcacatt    720
aattgcgttg cgctcactgc ccgctttcca gtcgggaaac cctgt                    765
```

<210> SEQ ID NO 42
<211> LENGTH: 984
<212> TYPE: DNA
<213> ORGANISM: Artificial Sequence
<220> FEATURE:
<223> OTHER INFORMATION: Recombinant polynucleotide

<400> SEQUENCE: 42

```
tagtaaatga attttctgta tgaggttttg ctaaacaact ttcaacagtc tatgcggccc     60
cctttccagt cggttcatct ctatgtctgt ataatgtgcg gccgaattca gatcctcttc    120
tgagatgagt ttttgttctg cggccgcgct cgagacggtg accagggttc cctgacccca    180
atacctcacc ttctggttcc aaagcgccct acctgtcgcg caataatata ccgcggtgtc    240
ctcggcacgc aggctgttca tttgcagata cagcgtgttc ttggaattgt cacgggagat    300
ggtgaaccgg cccttcacgg agtctgcgta gtatgtgcta ccgttaccgg tctgaatgct    360
tgatacccac tctagaccct tccctggagc ctggcggacc cagcccatat tcttagggct    420
aaccctatct ccggaggctg cacaggagag acgcaggacc ccccaggct gtaccaagcc    480 tcccccagac tccaacagct gcacctgggc catggccggc tgggccgcat agaaaggtac    540
cactaaagga attgcgaata ataatttttt cattatgact gtctccttga aatagaattt    600
gcatgcaagc ttggcgtaat catggtcata gctgtttcct gtgtgaaatt gttatccgct    660
cacaattcca cacaacatac gagccggaag cataaagtgt aaagcctggg gtgcctaatg    720
agtgagctaa ctcacattaa ttgcgttgcg ctcactgccc gctttccagt cgggaacctg    780
ttcgtgccag ctgcattaat gaatcggcc aacgcgcggg gagaggcgg tttgcgtatt    840 gggcgctctt ccgcttcctc gctcactgac tcgctgcgct cggacgttcg gctgcggcga    900
gcggtaccag ctcactcaaa ggcggtaata cggttatcca cagaatcagg ggataacgca    960
gcgaaagaac atgtgagcaa aagg                                          984
```

<210> SEQ ID NO 43
<211> LENGTH: 850
<212> TYPE: DNA
<213> ORGANISM: Artificial Sequence
<220> FEATURE:
<223> OTHER INFORMATION: Recombinant polynucleotide

<400> SEQUENCE: 43

```
aatgaatttt ctgtatgagg ttttgctaaa caactttcac agtctatgcg gccccctttc     60
caagtcggtt catctctatg tctgtataat gtgcggccga attcagatcc tcttctgaga    120
tgagtttttg ttctgcggcc gcgctcgaga cggtgaccag ggttccctga ccccaatacg    180
gcaactggtt ctacatcatc ctcttaggac ccgcgcaata atataccgcg gtgtcctcgg    240
cacgcaggct gttcatttgc agatacgcg tgttcttgga attgtcacgg agatggtga    300 accggccctt cacggagtct gcgtagtatg tgctaccgtt tctggcacta atggttgata    360
cccactctag accccttccct ggagcctggc ggacccagcc catagcctaa gagctaagcc    420
taaatcggga ggctgcacag gagagacgca gggaccccc aggctatacc aagcctcccc    480
cagactccaa cagctgcacc tgggccatgg ccggctgggc cgcatagaaa ggtaccacta    540
```

```
aaggaattgc gaataataat tttttcatta tgactgtctc cttgaaatag aatttgcatg      600
caagcttggc gtaatcatgg tcatagctgt ttcctgtgtg aaattgttat ccgctcacaa      660
ttccacacaa catacgagcc gggaagcata agtgtaaag cctgggggtg cctaatgagt       720
gagctaactc accattaatt gcgttgcgct cactgcccgc tttccagtcg ggaaacctgt      780
cgtgccagct gcattaatga atcggcccac gcgcgggaga ggcggtttgc gtattgggcg      840
ctcttccgct                                                             850

<210> SEQ ID NO 44
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 44
atggcccagg tgcagctgtt ggagtctggg ggaggcttgg tacagcctgg ggggtccctt       60
cgtctctcct gtgcagcctc cggagttaag attagccatt agaatatggc ctgggtccgc      120
caggctccag ggaagggtct agagtgggta tcaagcattg gatgcgtag cggtagcaca       180 tactacgcag actccgtgaa gggccggttc accatctccc gtgacaattc caagaacacg      240
ctgtatctgc aaatgaacag cctgcgtgcc gaggacaccg cggtatatta ttgcgcgagt      300
tagaggcggt tgtcgtttcc gaacaagttc aagttttggg gtcagggaac cctggtcacc      360
gtctcgagcg cggccgcaga acaaaaactc atctcagaag aggatct                    407

<210> SEQ ID NO 45
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 45
atggcccagg tgcagctgtt ggagtctggg ggaggcttgg tacagcctgg ggggtccctg       60
cgtctctcct gtgcagcctc cggagttagg cttacccata agaatatggg ctgggtccgc      120
caggctccag ggaagggtct agagtgggta tcaagcattc gtggccgtga cggtagcaca      180
tactacgcag actccgtgaa gggccggttc accatctccc gtgacaattc caagaacacg      240
ctgtatctgc aaatgaacag cctgcgtgcc gaggacaccg cggtatatca ttgcgcgaga      300
ggtcggtagt atatgcgtcc gacgaccgtc cagtttttggg gtcagggaac cctggtcacc     360
gtctcgagcg cggccgcaga acaaaaactc atctcagaag aggatct                    407

<210> SEQ ID NO 46
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 46
atggcccagg tgcagctgtt ggagtctggg ggaggcttgg tacagcctgg ggggtccctg       60
cgtctctcct gtgcagcctc cggagttaac attatctatt aggatatggc ctgggtccgc      120
caggctccag ggaagggtct agagtgggta tcaaccattc gtacgcgaag cggtagcaca      180
taatacgcag actccgtgaa gggccggttc accatctccc gtgacaattc caagaacacg      240
```

```
ctgtatctgc aaatgaacag cctgcgtgcc gaggacaccg cggtatatta ttgcgcgggt    300
aggaggaggc gtaccgccaa cttccgctat tggggtcagg gaaccctggt caccgtctcg    360
agcgcggccg cagaacaaaa actcatctca gaagaggatc t                        401
```

```
<210> SEQ ID NO 47
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 47
atggcccagg tgcagctgtt ggagtctggg ggaggcttgg tacagcctgg ggggtccctg    60
cgtctctcct gtgcagcctc cggagttaag attagctatt agtctatggc ctgggtccgc    120
caggctccag ggaagggtct agagtgggta tcaagcattc tgatgcaaaa cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaca    300
acgagggtta ggcggccggc gaacatgaag tattggggtc agggaaccct ggtcaccgtc    360
tcgagcgcgc cgcagaaca aaaactcatc tcagaagagg atct                      404
```

```
<210> SEQ ID NO 48
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 48
atggcccagg tgcagctgtt ggagtctggg ggaggcttgg tacagcctgg ggggtccctg    60
cgtctctcct gtgcagcctc cggatatagg tttaactctt aggctatggg ctgggtccgc    120
caggctccag ggaagggtct agagtgggta tcaagcatta atatgcgagg cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaca    300
gttcctagga gtatgtggtg ggctggtctg actgcgaagc cgatcaggta ttggggtcag    360
ggaaccctgg tcaccgtctc gagcgcggcc gcagaacaaa aactcatctc agaagaggat    420
ct                                                                    422
```

```
<210> SEQ ID NO 49
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 49
atggcccagg tgcagctgtt ggagtctggg ggaggcttgg tacagcctgg ggggtccctg    60
cgtctctcct gtgcagcctc cggagttaag tttaccaatt agtatatggg ctgggtccgc    120
caggctccag ggaagggtct agagtgggta tcaagcatta tgacgcaaag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgggt    300
aggcgtggta agcggtggct tgtgtcgccg ctccggtatt ggggtcaggg aaccctggtc    360
accgtctcga gcgcggccgc agaacaaaaa ctcatctcag aagaggatct               410
```

<210> SEQ ID NO 50
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 50

```
atggcccagg tgcagctgtt ggagtctggg ggaggcttgg tacagcctgg ggggtccctg     60
cgtctctcct gtgcagcctc cggagttagg tttaaccatt agtttatgag ctgggtccgc    120
caggctccag ggaagggtct agagtgggta tcaggcatta atagccgaag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgagt    300
gcgcgtcggg cgccttttcg tacgaagtac atcaagtttt ggggtcaggg aaccctggtc    360
accgtctcga gcgcggccgc agaacaaaaa ctcatctcag aagaggatct              410
```

<210> SEQ ID NO 51
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 51

```
atggcccagg tgcagctgtt ggagtctggg ggaggcttgg tacagcctgg ggggtccctg     60
cgtctctcct gtgcagcctc cggagatagg tttagcaatt aggctatgag ctgggtccgc    120
caggctccag ggaagggtct agagtgggta tcaggcatta ataccacaga cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcggca    300
cctcggcgtt tgaggggtag gccttggtct gtgcccaca  agatggggtt ttggggtcag    360
ggaaccctgg tcaccgtctc gagcgcggcc gcagaacaaa aactcatctc agaagaggat    420
ct                                                                   422
```

<210> SEQ ID NO 52
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 52

```
atggcccagg tgcagctgtt ggagtctggg ggaggcttgg tacagcctgg ggggtccctg     60
cgtctctcct gtgcagcctc cggatttagg tttagccatt agtatatggg ctgggtccgc    120
caggctccag ggaagggtct agagtgggta tcaaccattg ctatgactaa cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaga    300
tggcatgggg ggaggaagtg gccgaagccc ttgacgtctt ggggtcaggg aaccctggtc    360
accgtctcga gcgcggccgc agaacaaaaa ctcatctcag aagaggatct              410
```

<210> SEQ ID NO 53
<211> LENGTH: 407
<212> TYPE: DNA

<213> ORGANISM: Artificial Sequence
<220> FEATURE:
<223> OTHER INFORMATION: Recombinant polynucleotide

<400> SEQUENCE: 53

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatatagg | tttaacgatt | agactatggc | ctgggtccgc | 120 |
| caggctccag | ggaagggtct | agagtgggta | tcaaccattg | tgccactaa | cggtagcaca | 180 |
| tactacgcag | actccgtgaa | gggccggttc | accatctccc | gtgacaattc | caagaacacg | 240 |
| ctgtatctgc | aaatgaacag | cctgcgtgcc | gaggacaccg | cggtatatta | ttgcgcgaga | 300 |
| cggcgtaggc | ttggtgcttc | gcactacatg | cggttttggg | gtcagggaac | cctggtcacc | 360 |
| gtctcgagcg | cggccgcaga | acaaaaactc | atctcagaag | aggatct | | 407 |

<210> SEQ ID NO 54
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 54

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatataag | tttaactctc | actatatgag | ctgggtccgc | 120 |
| caggctccag | ggaagggtct | agagtgggta | tcaaccatta | ggaaccgtga | cggtagcaca | 180 |
| tactacgcag | actccgtgaa | gggccggttc | accatctccc | gtgacaattc | caagaacacg | 240 |
| ctgtatctgc | aaatgaacag | cctgcgtgcc | gaggacaccg | cggtatatta | ttgcgcgaga | 300 |
| taggcgaggc | agcggccgac | caacttctac | tcttggggtc | agggaaccct | ggtcaccgtc | 360 |
| tcgagcgcgg | ccgcagaaca | aaaactcatc | tcagaagagg | atct | | 404 |

<210> SEQ ID NO 55
<211> LENGTH: 413
<212> TYPE: DNA
<213> ORGANISM: Artificial Sequence
<220> FEATURE:
<223> OTHER INFORMATION: Recombinant polynucleotide

<400> SEQUENCE: 55

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | aggatttagg | gttatccta | agtatatggg | ctgggtccgc | 120 |
| caggctccag | ggaagggtct | agagtgggta | tcaaccatta | agacccgtga | cggtagcaca | 180 |
| tactacgcag | actccgtgaa | gggccggttc | accatctccc | gtgacaattc | caagaacacg | 240 |
| ctgtatctgc | aaatgaacag | cctgcgtgcc | gaggacaccg | cggtatatta | ttgcgcgaga | 300 |
| gttaataggt | ggaggttggc | gactcccaac | taggtcgagt | cttggggtca | gggaaccctg | 360 |
| gtcaccgtct | cgagcgcggc | cgcagaacaa | aaactcatct | cagaagagga | tct | 413 |

<210> SEQ ID NO 56
<211> LENGTH: 425
<212> TYPE: DNA
<213> ORGANISM: Artificial Sequence
<220> FEATURE:
<223> OTHER INFORMATION: Recombinant polynucleotide

<400> SEQUENCE: 56

| | | | | | |
|---|---|---|---|---|---|
| atggcccagg | tgcagctgtt | ggagtctggg | ggaggcttgg | tacagcctgg | ggggtccctg | 60 |

```
cgtctctcct gtgcagcctc cggatttatg cttaacaatt aggatatgag ctgggtccgc    120
caggctccag ggaagggtct agagtgggta tcagccattc gtgccccaag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaga    300
aagaagggga tggggaggtt tccgggtatg atgaggaagc cgcacatgcg cttttggggt    360
cagggaaccc tggtcaccgt ctcgagcgcg ccgcagaac aaaaactcat ctcagaagag    420
gatct                                                                425

<210> SEQ ID NO 57
<211> LENGTH: 431
<212> TYPE: DNA
<213> ORGANISM: Artificial Sequence
<220> FEATURE:
<223> OTHER INFORMATION: Recombinant polynucleotide

<400> SEQUENCE: 57
atggcccagg tgcagctgtt ggagtctggg ggaggcttgg tacagcctgg ggggtccctg     60
cgtctctcct gtgcagcctc cggagttacg attaacaatt agtatatggg ctgggtccgc    120
caggctccag ggaagggtct agagtgggta tcaagcattc ggaaccgtaa cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgagt    300
tgtgggagga ggcgttgtcg gtatcggggg ggggattatc agcacaagtc gatgaggtat    360
tggggtcagg gaaccctggt caccgtctcg agcgcggccg cagaacaaaa actcatctca    420
gaagaggatc t                                                          431

<210> SEQ ID NO 58
<211> LENGTH: 419
<212> TYPE: DNA
<213> ORGANISM: Artificial Sequence
<220> FEATURE:
<223> OTHER INFORMATION: Recombinant polynucleotide

<400> SEQUENCE: 58
atggcccagg tgcagctgtt ggagtctggg ggaggcttgg tacagcctgg ggggtccctg     60
cgtctctcct gtgcagcctc cggatttaag tttagcgctt agtatatgag ctgggtccgc    120
caggctccag ggaagggtct agagtgggta tcaaccatta agatgaataa cggtagcaca    180
tactacgcag actccgtgaa gggccggttc accatctccc gtgacaattc caagcacacg    240
ctgtatctgc aaatgaacag cctgcgtgcc gaggacaccg cggtatatta ttgcgcgaga    300
ccgatggcgt ggcggggtaa tgtggtgcgg gccgagaact gcggttttg gggtcaggga    360 accctggtca ccgtctcgag cgcggccgca gaacaaaaac tcatctcaga agaggatct    419

<210> SEQ ID NO 59
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 59
atggcccagg tgcagctgtt ggagtctggg gaaggcttgg tacagcctgg ggggtccctg     60
cgtctctcct gtgcagcctc cggagttagg cttacccata gaatatggg ctgggtccgc     120
```

| | |
|---|---|
| caggctccag ggaagggtct agagtgggta tcaagcattc gtggccgtga cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatca ttgcgcgaga | 300 |
| ggtcggtagt atatgcgtcc gacgaccgtc cagttttggg gtcagggaac cctggtcacc | 360 |
| gtctcgagcg cggccgcaga acaaaaactc atctcagaag aggatct | 407 |

<210> SEQ ID NO 60
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 60

| | |
|---|---|
| atggcccagg tgcagctgtt ggagtctggg ggaggcttgg tacagcctgg ggggtccctg | 60 |
| cgtctctcct gtgcagcctc cggagttaag cttagccatt agaatatggg ctgggtccgc | 120 |
| caggctccag ggaagggtct agagtgggta tcaagcattg gtatccgtag cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatca ttgcgcgaga | 300 |
| ggtcggtggt atttgtgtcc gaccacgtc cagttttggg gtcagggaac cctggtcacc | 360 |
| gtctcgagcg cggccgcaga acaaaaactc atctcagaag aggatct | 407 |

<210> SEQ ID NO 61
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 61

| | |
|---|---|
| atggcccagg tgcagctgtt ggagtctggg ggaggcttgg tacagcctgg ggggtccctt | 60 |
| cgtctctcct gtgcagcctc cggagttaag attagccgtt agaatatggc ctgggtccgc | 120 |
| caggctccag ggaagggtct agagtgggta tcaagcattg gatgcgtag cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcgagt | 300 |
| tagaggcggt tgtcgtttcc gaacaagttc aagttttggg gtcagggaac cctggtcacc | 360 |
| gtctcgagcg cggccgcaga acaaaaactc atctcagaag aggatct | 407 |

<210> SEQ ID NO 62
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 62

| | |
|---|---|
| atggcccagg tgcagctgtt ggagtctggg ggaggcttgg tacagcctgg ggggtccctg | 60 |
| cgtctctcct gtgcagcctc cggagttagg gttagctata aggctatgag ctgggtccgc | 120 |
| caggctccag ggaagggtct agagtgggta tcaaccattc agaacaaaaa cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcgaca | 300 |
| aagcgggctt gggttaacaa cacgttccgg tattggggtc agggaaccct ggtcaccgtc | 360 |

```
tcgagcgcgg ccgcagaaca aaaactcatc tcagaagagg atct            404
```

<210> SEQ ID NO 63
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 63

```
atggcccagg tgcagctgtt ggagtctggg ggaggcttgg tacagcctgg ggggtccctg     60
cgtctctcct gtgcagcctc cggatatagc tttaactatt agtatatggg ctgggtccgc    120
caggctccag ggaagggtct agagtgggta tcaaccattc gtaagcgtga cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaga    300
cggaaggggc ggcggaatag tgaggagggt cagacgtcct ccttgtggtc ttggggtcag    360
ggaaccctgg tcaccgtctc gagcgcggcc gcagaacaaa aactcatctc agaagaggat    420
ct                                                                   422
```

<210> SEQ ID NO 64
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 64

```
atggcccagg tgcagctgtt ggagtctggg ggaggcttgg tacagcctgg ggggtccctt     60
cgtctctcct gtgcagcctc cggagttaag attagccatt agaatatggc ctgggtccgc    120
caggctccag ggaagggtct agagtgggta tcaagcattg gatgcgtag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgagt    300
tagaggcggt tgtagtttcc gaacaagttc aagtttggg gtcagggaac cctggtcacc    360
gtctcgagcg cggccgcaga acaaaaactc atctcagaag aggatct                  407
```

<210> SEQ ID NO 65
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 65

```
atggcccagg tgcagctgtt ggagtctggg ggaggcttgg tacagcctgg ggggtccctg     60
cgtctctcct gtgcagcctc cggatttaag gttatctctt agaatatggc ctgggtccgc    120
caggctccag ggaagggtct agagtgggta tcaagcattg gtagccatga cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgagt    300
agggttcgtc atcggaatga gttgaataat attaagtccg agttgcggtc ttggggtcag    360
ggaaccctgg tcaccgtctc gagcgcggcc gcagaacaaa aactcatctc agaagaggat    420
ct                                                                   422
```

<210> SEQ ID NO 66
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 66

```
atggcccagg tgcagctgtt ggagtctggg ggaggcttgg tacagcctgg ggggtccctg      60
cgtctctcct gtgcagcctc cggagttaag tttaccaatt agtttatggc ctgggtccgc     120
caggctccag ggaagggtct agagtgggta tcaaccattc agacgaaaaa cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaga     300
aggcggtggc cgtgggtgaa gaaccccacc atgtactttt ggggtcaggg aaccctggtc     360
accgtctcga gcgcggccgc agaacaaaaa ctcatctcag aagaggatct              410
```

<210> SEQ ID NO 67
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 67

```
attgcccagg tgcagctgtt ggagtctggg ggaggcttgg tacagcctgg ggggtccctg      60
cgtctctcct gtgcagcctc cggatttacg tttagctata acaatatggc ctgggtccgc     120
caggctccag ggaagggtct agagtgggta tcagccattt aggggaaaga cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaga     300
cgtaaggggc gtacggagaa gctgtcgtat tggggtcagg gaaccctggt caccgtctcg     360
agcgcggccg cagaacaaaa actcatctca gaagaggatc t                         401
```

<210> SEQ ID NO 68
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 68

```
atggcccagg tgcagctgtt ggagtctggg ggaggcttgg tacagcctgg ggggtccctg      60
cgtctctcct gtgcagcctc cggagttaag tttaaccctt aggctatggg ctgggtccgc     120
caggctccag ggaagggtct agagtgggta tcagccattg gtgcgacaga cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaga     300
gggcgtttgg gtttgcatgg accgccaag atgaggtctt ggggtcaggg aaccctggtc      360
accgtctcga gcgcggccgc agaacaaaaa ctcatctcag aagaggatct              410
```

<210> SEQ ID NO 69
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 69

```
atggcccagg tgcagctgtt ggagtctggg ggaggcttgg tacagcctgg ggggtccctg      60
cgtctctcct gtgcagcctc cggagttaac gttaccaatt aggttatgac ctgggtccgc     120
caggctccag ggaagggtct agagtgggta tcaaccattc ttggcagaaa cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaca     300
cggttggggc gtaggaagcc cgcctaggtg cggtcttggg gtcagggaac cctggtcacc     360
gtctcgagcg cggccgcaga acaaaaactc atctcagaag aggatct                   407
```

<210> SEQ ID NO 70
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 70

```
atggcccagg tgcagctgtt ggagtctggg ggaggcttgg tacagcctgg ggggtccctg      60
cgtctctcct gtgcagcctc cggatatagg tttaacactt aggatatggg ctgggtccgc     120
caggctccag ggaagggtct agagtgggta tcaaccattg ctatcggaag cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgggt     300
aggaggaggc gtaccgccaa cttccgctat tggggtcagg aaccccggt caccgtctcg      360 agcgcggccg cagaacaaaa actcatctca gaagaggatc t                         401
```

<210> SEQ ID NO 71
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 71

```
atggcccagg tgcagctgtt ggagtctggg ggaggcttgg tacagcctgg ggggtccctg      60
cgtctctcct gtgcagcctc cggagatagc gttaacactt agattatggg ctgggtccgc     120
caggctccag ggaagggtct agagtgggta tcaaccattg ttaagcgaga cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaca     300
cgtcgtctta gaacccagca gttgcgctat tggggtcagg aaccctggt caccgtctcg      360 agcgcggccg cagaacaaaa actcatctca gaagaggatc t                         401
```

<210> SEQ ID NO 72
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 72

```
atggcccagg tgcagctgtt ggagtctggg ggaggcttgg tacagcctgg ggggtccctg      60
cgtctctcct gtgcagcctc cggagttaac gttagcaatt aggttatgag ctgggtccgc     120
```

| | |
|---|---|
| caggctccag ggaagggtct agagtgggta tcaaccattg ctaaccatag cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcgagt | 300 |
| actgggcgtc gtccctagaa ggtgcagtct tggggtcagg gaaccctggt caccgtctcg | 360 |
| agcgcggccg cagaacaaaa actcatctca gaagaggatc t | 401 |

<210> SEQ ID NO 73
<211> LENGTH: 416
<212> TYPE: DNA
<213> ORGANISM: Artificial Sequence
<220> FEATURE:
<223> OTHER INFORMATION: Recombinant polynucleotide

<400> SEQUENCE: 73

| | |
|---|---|
| atggcccagg tgcagctgtt ggagtctggg ggaggcttgg tacagcctgg ggggtccctg | 60 |
| cgtctctcct gtgcagcctc cggagttaac attagcgctt aggttatgac ctgggtccgc | 120 |
| caggctccag ggaagggtct agagtgggta tcaaccattt gaacagaga cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcggga | 300 |
| aatcgggagg ggaataagcg ttaggtgacg cagtcgatcc agtcttgggg tcaggaacc | 360 |
| ctggtcaccg tctcgagcgc ggccgcagaa caaaaactca tctcagaaga ggatct | 416 |

<210> SEQ ID NO 74
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 74

| | |
|---|---|
| atggcccagg tgcagctgtt ggagtctggg ggaggcttgg tacagcctgg ggggtccctg | 60 |
| cgtctctcct gtgcagcctc cggagatagc cttatcccta gtatatgag ctgggtccgc | 120 |
| caggctccag ggaagggtct agagtgggta tcaggcattt agaccaatag cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcgaga | 300 |
| acgtcgcgga agaggacgac gccggtgcag tcttggggtc agggaaccct ggtcaccgtc | 360 |
| tcgagcgcgg ccgcagaaca aaaactcatc tcagaagagg atct | 404 |

<210> SEQ ID NO 75
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 75

| | |
|---|---|
| atggcccagg tgcagctgtt ggagtctggg ggaggcttgg tacagcctgg ggggtccctg | 60 |
| cgtctctcct gtgcagcctc cggatttacg tttatccata gtatatgag ctgggtccgc | 120 |
| caggctccag ggaagggtct agagtgggta tcaaccattt agagcagaag cggtagcaca | 180 |
| tactacgcag actccgtgaa gggccggttc accatctccc gtgacaattc caagaacacg | 240 |
| ctgtatctgc aaatgaacag cctgcgtgcc gaggacaccg cggtatatta ttgcgcgaga | 300 |
| gggaagaagc gtagtacgac caagcccatg cagtcttggg gtcaggaac cctggtcacc | 360 | gtctcgagcg cggccgcaga acaaaaactc atctcagaag aggatct         407

<210> SEQ ID NO 76
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 76
atggcccagg tgcagctgtt ggagtctggg ggaggcttgg tacagcctgg ggggtccctg    60
cgtctctcct gtgcagcctc cggatatacg gttaactatt agattatgac ctgggtccgc   120
caggctccag ggaagggtct agagtgggta tcaaccatta tgggcaaaga cggtagcaca   180
tactacgcag actccgtgaa gggccggttc accatctccc gtgacaattc caagaacacg   240
ctgtatctgc aaatgaacag cctgcgtgcc gaggacaccg cggtatatta ttgcgcggga   300
aagcggaata gtgattacaa gacggtcccg tattggggtc agggaaccct ggtcaccgtc   360
tcgagcgcgg ccgcagaaca aaaactcatc tcagaagagg atct              404

<210> SEQ ID NO 77
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 77
atggcccagg tgcagctgtt ggagtctggg ggaggcttgg tacagcctgg ggggtccctg    60
cgtctctcct gtgcagcctc cggatttatg gttaaccatt agaatatgag ctgggtccgc   120
caggctccag ggaagggtct agagtgggta tcaaccattg gtggccatga cggtagcaca   180
tactacgcag actccgtgaa gggccggttc accatctccc gtgacaattc caagaacacg   240
ctgtatctgc aaatgaacag cctgcgtgcc gaggacaccg cggtatatta ttgcgcggga   300
aggaggtcga ggggtgattt gacgcacccc ttgaagtttt ggggtcaggg aaccctggtc   360
accgtctcga gcgcggccgc agaacaaaaa ctcatctcag aaggagatct             410

<210> SEQ ID NO 78
<211> LENGTH: 416
<212> TYPE: DNA
<213> ORGANISM: Artificial Sequence
<220> FEATURE:
<223> OTHER INFORMATION: Recombinant polynucleotide

<400> SEQUENCE: 78
atggcccagg tgcagctgtt ggagtctggg ggaggcttgg tacagcctgg ggggtccctg    60
cgtctctcct gtgcagcctc cggatatagg tttagcaatt agactatggc ctgggtccgc   120
caggctccag ggaagggtct agagtgggta tcaacaatta ggaacccaga cggtagcaca   180
tactacgcag actccgtgaa gggccggttc accatctccc gtgacaattc caagaacacg   240
ctgtatctgc aaatgaacag cctgcgtgcc gaggacaccg cggtatatta ttgcgcgaca   300
cttaggaggt tgttggaggg ggctaggcag acgaaggtga ggtcttgggg tcagggaacc   360
ctggtcaccg tctcgagcgc ggccgcagaa caaaaactca tctcagaaga ggatct       416

<210> SEQ ID NO 79
<211> LENGTH: 404
<212> TYPE: DNA

```
<213> ORGANISM: Artificial Sequence
<220> FEATURE:
<223> OTHER INFORMATION: Recombinant polynucleotide

<400> SEQUENCE: 79
atggcccagg tgcagctgtt ggagtctggg ggaggcttgg tacagcctgg ggggtccctg      60
cgtctctcct gtgcagcctc cggagatagg gttagcccta gaatatgggc tgggtccgc     120 caggctccag ggaagggtct agagtgggta tcaagcattc agaccggtaa cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaca     300
ggtagggcgc tttggaacca aaggtgagg tattggggtc agggaaccct ggtcaccgtc     360
tcgagcgcgg ccgcagaaca aaaactcatc tcagaagagg atct                      404

<210> SEQ ID NO 80
<211> LENGTH: 404
<212> TYPE: DNA
<213> ORGANISM: Artificial Sequence
<220> FEATURE:
<223> OTHER INFORMATION: Recombinant polynucleotide

<400> SEQUENCE: 80
atggcccagg tgcagctgtt ggagtctggg ggaggcttgg tatagcctgg ggggtccctg      60
cgtctctcct gtgcagcctc cggatttagg cttagctctt aggctatggg ctgggtccgc     120
caggctccag ggaagggtct agagtgggta tcaaccatta gtgccagaaa cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgggt     300
cctaagagga tgatgtagaa ccagttgccg tattggggtc agggaaccct ggtcaccgtc     360
tcgagcgcgg ccgcagaaca aaaactcatc tcagaagagg atct                      404

<210> SEQ ID NO 81
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 81
atggcccagg tgcagctgtt ggagtctggg ggaggcttgg tacagcctgg ggggtccctg      60
cgtctctcct gtgcagcctc cggatataag tttagcgatt aggctatgag ctgggtccgc     120
caggctccag ggaagggtct agagtgggta tcagccattt atgtgcatga cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcgaga     300
tggcaggatc tgctgatgta ggaggaggcg ttgccctatt ggggtcaggg aaccctggtc     360
accgtctcga gcgcggccgc agaacaaaaa ctcatctcag aagaggatct                410

<210> SEQ ID NO 82
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 82
atggcccagg tgcagctgtt ggagtctggg ggaggcttgg tacagcctgg ggggtccctg      60
```

```
cgtctctcct gtgcagcctc cggatatatc tttagcgatt aggctatggg ctgggtccgc      120
caggctccag ggaagggtct agagtgggta tcaagcatta taccgcaaa cggtagcaca       180 tactacgcag actccgtgaa gggccggttc accatctccc gtgacaattc caagaacacg      240
ctgtatctgc aaatgaacag cctgcgtgcc gaggacaccg cggtatatta ttgcgcgggt      300
tatagtgagt ggtaggacga gatgcagtat tggggtcagg gaaccctggt caccgtctcg      360
agcgcggccg cagaacaaaa actcatctca gaagaggatc t                         401
```

<210> SEQ ID NO 83
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 83

```
atggcccagg tgcagctgtt ggagtctggg ggaggcttgg tacagcctgg ggggtccctg       60
cgtctctcct gtgcagcctc cggatataag tttagcgatt aggctatgag ctgggtccgc      120
caggctccag ggaagggtct agagtgggta tcagccattt atgtgcatga cggtagcaca      180
tactacgcag actccgtgaa gggccggttc accatctccc gtgacaattc caagaacacg      240
ctgtatctgc aaatgaacag catgcgtgcc gaggacaccg cggtatatta ttgcgcgaga      300
tggcaggatc agctgatgta ggaggaggcg ttgccctatt ggggtcaggg aaccctggtc      360
accgtctcga gcgcggccgc agaacaaaaa ctcatctcag aagaggatct                 410
```

<210> SEQ ID NO 84
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 84

```
atggcccagg tgcagctgtt ggagtctggg ggaggcttgg tacagcctgg ggggtccctg       60
cgtctctcct gtgcagcctc cggatataag tttagcgatt aggctatgag ctgggtccgc      120
caggctccag ggaagggtct agagtgggta tcagccattt atgtgcatga cggtagcaca      180
tactacgcag actccgtgaa gggccggttc accatctccc gtgacaattc caagaacacg      240
ctgtatctgc aaatgaacag catgcgtgcc gaggacaccg cggtatatta ttgcgcgaga      300
tggcaggatc tgctgatgta ggaggaggcg ttgccctatt ggggtcaggg aaccctggtc      360
accgtctcga gcgcggccgc agaacaaaaa ctcatctcag aagaggatct                 410
```

<210> SEQ ID NO 85
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 85

```
atggcccagg tgcagctgtt ggagtctggg ggaggcttgg tacagcctgg ggggtccctg       60
cgtctctcct gtgcagcctc cggatataag tttagcgatt aggctatgag ctgggtccgc      120
caggctccag ggaagggtct agagtgggta tcagccattt atgtgcatga cggtagcaca      180
tactacgcag actccgtgaa gggccggttc accatctccc gtgacaattc caagaacacg      240
```

```
ctgtatctgc aaatgaacag catgcgtgcc aggacaccg cggtatatta ttgcgcgaga    300
tggcaggatc tgatgatgta ggaggaggcg ttgccctatt ggggtcaggg aaccctggtc    360
accgtctcga gcgcggccgc agaacaaaaa ctcatctcag aagaggatct              410
```

<210> SEQ ID NO 86
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 86

```
atggcccagg tgcagctgtt ggagtctggg ggaggcttgg tacagcctgg ggggtccctg    60
cgtctctcct gtgcagcctc cggagttaca tttaacgatg agtttatgac ctgggtccgc    120
caggctccag ggaagggtct agagtgggta tcaaccatta gtaaccgtaa cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgggt    300
gatttgttgg gtcccgcgcc ggtgggctct tggggtcagg aaccctggt caccgtctcg    360 agcgcggccg cagaacaaaa actcatctca gaagaggatc t                       401
```

<210> SEQ ID NO 87
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 87

```
atggcccagg tgcagctgtt ggagtctggg ggaggcttgg tacagcctgg ggggtccctg    60
cgtctctcct gtgcagcctc cggatataag tttagcgatt aggctatgag ctgggtccgc    120
caggctccag ggaagggtct agagtgggta tcagccattt atgtgcatga cggtagcaca    180
tcctacgcag actccgtgaa gggccggttc accatctccc gtgacaattc caagaacacg    240
ctgtatctgc aaatgaacag cctgcgtgcc gaggacaccg cggtatacta ttgcgcgaga    300
tggcaggatc atctgatgta gtaggaggcg atgccctatt ggggtcaggg aaccctggtc    360
accgtctcga gcgcggccgc agaacaaaaa ctcatctcag aagaggatct              410
```

<210> SEQ ID NO 88
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 88

```
atggcccagg tgcagctgtt ggagtctggg ggaggcttgg tacagcctgg ggggtccctg    60
cgtctctcct gtgcagcctc cggatataag tttagcgatt aggctatgag ctgggtccgc    120
caggctccag ggaagggtct agagtgggta tcagccattt atgtgcatga cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaga    300
tggcaggatc atctgatgta ggaggaggcg atgccctatt ggggtcaggg aaccctggtc    360
accgtctcga gcgcggccgc agaacaaaaa ctcatctcag aagaggatct              410
```

<210> SEQ ID NO 89
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 89

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatataag | tttagcgatt | aggctatgag | ctgggtccgc | 120 |
| caggctccag | ggaagggtct | agagtgggta | tcagccattt | atgtgcatga | cggtagcaca | 180 |
| tactacgcag | actccgtgaa | gggccggttc | accatctccc | gtgacaattc | caagaacacg | 240 |
| ctgtatctgc | aaatgaacag | catgcgtgcc | gaggacaccg | cggtatacta | ttgcgcgaga | 300 |
| tggcaggatc | atcttatgta | ggaggaggag | atgccctatt | ggggtcaggg | aaccctggtc | 360 |
| accgtctcga | gcgcggccgc | agaacaaaaa | ctcatctcag | aagaggatct | | 410 |

<210> SEQ ID NO 90
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 90

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatataag | tttagcgatt | aggctatgag | ctgggtccgc | 120 |
| caggctccag | ggaagggtct | agagtgggta | tcagccattt | atgtgcatga | cggtagcaca | 180 |
| tattacgcag | actccgtgaa | gggccggttc | accatgttcc | gtgacaattc | caagaacacg | 240 |
| ctgtatctgc | agatgaacag | catgcgtgcc | gaggacaccg | cggtatatta | ttgcgcgaga | 300 |
| tggcaggatc | agatgatgta | ggaggaggcg | ttgccctatt | ggggtcaggg | aaccctggtc | 360 |
| accgtctcga | gcgcggccgc | agaacaaaaa | ctcatctcag | aagaggatct | | 410 |

<210> SEQ ID NO 91
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 91

| | | | | | |
|---|---|---|---|---|---|
| atggcccagg | tgcagctgtt | ggagtctggg | ggaggcttgg | tacagcctgg | ggggtccctg | 60 |
| cgtctctcct | gtgcagcctc | cggatataag | tttagcgatt | aggctatgag | ctgggtccgc | 120 |
| caggctccag | ggaagggtct | agagtgggta | tcagccattt | atgtgcatga | cggtagcaca | 180 |
| tattacgcag | actccgtgaa | gggccggttc | accatcttcc | gtgacaattc | caagaacacg | 240 |
| ctgtatctgc | agatgaacag | catgcgtgcc | gaggacaccg | cggtatatta | ttgcgcgaga | 300 |
| tggcaggatc | tgatgatgta | ggaggaggcg | ttgccctatt | ggggtcaggg | aaccctggtc | 360 |
| accgtctcga | gcgcggccgc | agaacaaaaa | ctcatctcag | aagaggatct | | 410 |

<210> SEQ ID NO 92
<211> LENGTH: 410
<212> TYPE: DNA
<213> ORGANISM: Artificial Sequence
<220> FEATURE:
<223> OTHER INFORMATION: Recombinant polynucleotide

```
<400> SEQUENCE: 92
atggcccagg tgcagctgtt ggagtctggg ggaggcttgg tacagcctgg ggggtccctg      60
cgtctctcct gtgcagcctc cggatataag tttagcgatt aggctatgag ctgggtccgc     120
caggctccag ggaagggtct agagtgggta tcagccattt atgtgcatga cggtagcaca     180
tactacgcag actccgtgaa gggccggttc accatctccc gtgacaattc caagaacacg     240
ctgtatctgc aaatgaacag catgcgtgcc gaggacaccg cggtatatta ttgcgcgaga     300
tggcaggatc ttcttatgta ggaggaggcg ttgccctatt ggggtcaggg aaccctggtc     360
accgtctcga gcgcggccgc agaacaaaaa ctcatctcag aagaggatct                410

<210> SEQ ID NO 93
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 93
atggcccagg tgcagctgtt ggagtctggg ggaggcttgg tacagcctgg ggggtccctg      60
cgtctctcct gtgcagcctc cggatataag tttagcgatt aggctatgag ctgggtccgc     120
caggctccag ggaagggtct agagtgggta tcagccattt atgtgcatga cggtagcaca     180
tactacgcag actccgtgaa gggccggttc accatctccc gtgacaattc caagaacacg     240
ctgtatctgc aaatgaacag catgcgtgcc gaggacaccg cggtatatta ttgcgcgaga     300
tggcaggatc tgattatgta ggaggaggcg ttgccctatt ggggtcaggg aaccctggtc     360
accgtctcga gcgcggccgc agaacaaaaa ctcatctcag aagaggatct                410

<210> SEQ ID NO 94
<211> LENGTH: 410
<212> TYPE: DNA
<213> ORGANISM: Artificial Sequence
<220> FEATURE:
<223> OTHER INFORMATION: Recombinant polynucleotide

<400> SEQUENCE: 94
atggcccagg tgcagctgtt ggagtctggg ggaggcttgg tacagcctgg ggggtccctg      60
cgtctctcct gtgcagcctc cggatataag tttagcgatt aggctatgag ctgggtccgc     120
caggctccag ggaagggtct agagtgggta tcagccattt atgtgcatga cggtagcaca     180
tattacgcag actccgtgaa gggccggttc accatctccc gtgacaattc caagaacacg     240
ctgtatctgc aaatgaacag catgcgtgcc gaggacaccg cggtatatta ttgcgcgaga     300
tggcaggatc agatgatgta ggaggaggcg ttgccctatt ggggtcaggg aaccctggtc     360
accgtctcga gcgcggccgc agaacaaaaa ctcatctcag aagaggatct                410

<210> SEQ ID NO 95
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 95
atggcccagg tgcagctgtt ggagtctggg ggaggcttgg tacagcctgg ggggtccctg      60
cgtctctcct gtgcagcctc cggatttaag attatcgatt acgatatggg ctgggtccgc     120
caggctccag ggaagggtct agagtgggta tcaagcattt agaacagaag cggtagcaca     180
```

```
tactacgcag actccgtgaa gggccggttc accatctccc gtgacaattc caagaacacg    240
ctgtatctgc aaatgaacag cctgcgtgcc gaggacaccg cggcatatta ttgcgcgggt    300
tatgggaggt aggacgagac ggtcgactat tggggtcagg gaaccctggt caccgtctcg    360
agcgcggccg cagaacaaaa actcatctca gaagaggatc t                       401

<210> SEQ ID NO 96
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 96
atggcccagg tgcagctgtt ggagtctggg ggaggcttgg tacagcctgg ggggtccctg     60
cgtctctcct gtgcagcctc cggatatatg attagcgatt agtatatggg ctgggtccgc    120
caggctccag ggaagggtct agagtgggta tcaggcattg ataccagtag cggtagcaca    180
tactacgcag actccgtgaa gggccggttc accatctccc gtgacaattc caagaacacg    240
ctgtatctgc aaatgaacag cctgcgtgcc gaggacaccg cggtatatta ttgcgcgaca    300
ctgctttctt cggaccccaa cgtcaactat tggggtcagg gaaccctggt caccgtctcg    360
agcgcggccg cagaacaaaa actcatctca gaagaggatc t                       401

<210> SEQ ID NO 97
<211> LENGTH: 335
<212> TYPE: DNA
<213> ORGANISM: Artificial Sequence
<220> FEATURE:
<223> OTHER INFORMATION: Recombinant polynucleotide

<400> SEQUENCE: 97
tcctgtgcag cctccggata tatctttaga gattaggcta tgggctgggt ccgccaggct     60
ccagggaagg gtctagagtg gtatcaagc attcataccg caaacggtag cacatactac    120
gcagactccg tgaagggccg gttcaccatc tcccgtgaca attccaagaa cacgctgtat    180
ctgcaaatga acagcctgcg tgccgaggac accgcgtat attattgcgc gggttatagt    240
gagtggtagg acgagatgca gtattggggt cagggaaccc tggtcaccgt ctcgagcgcg    300
gccgcagaac aaaaactcat ctcagaagag gatct                              335

<210> SEQ ID NO 98
<211> LENGTH: 377
<212> TYPE: DNA
<213> ORGANISM: Artificial Sequence
<220> FEATURE:
<223> OTHER INFORMATION: Recombinant polynucleotide

<400> SEQUENCE: 98
aggcttggta cagcttgggg ggtccctgcg tctctcctgt gcagcctccg gatataagtt     60
tagcgattag gctatgagct gggtccgcca ggctccaaga agggtctaga gtgggtatca    120
gccatttatg tgcatgacgg tagcacatac tacgcagact ccgtgaaggg ccggttcacc    180
atgttccgtg tcaattccaa gaacacgctg tatctgcaaa tgaacagcat gcgtgccgag    240
gacaccgcgg tatattattg cgcgagatgg caggatcata tgatgtagga ggaggcgttg    300
ccctattggg gtcagggaac cctggtcacc gtctcgagcg cggccgcaga acaaaaactc    360
atctcagaag aggatct                                                  377
```

<210> SEQ ID NO 99
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 99

| | | |
|---|---|---|
| atggcccagg tgcagctgtt ggagtctggg ggaggcttgg tacagcctgg ggggtccctg | 60 |
| cgtctatcct gtgcagcctc cggatatatc tttagcgatt aggctatggg ctgggtccgc | 120 |
| caggctccag gaagggtct agagtgggta tcaagcattc aaaccgcaaa cggtagcacc | 180 |
| tcctccgcag actccgtgaa gggccggttc accatctccc gtgacaattc caagaacacg | 240 |
| ctgtatctgc aaatgaacag cctgcgtgcc gaggacaccg cggtatatta ttgcgcgggt | 300 |
| tatagtgagt ggtaggacga gatgcagtat tggggtcagg gaaccctggt caccgtatcg | 360 |
| agcgcggccg cagaacaaaa actcatctct ttagaggatc t | 401 |

<210> SEQ ID NO 100
<211> LENGTH: 359
<212> TYPE: DNA
<213> ORGANISM: Artificial Sequence
<220> FEATURE:
<223> OTHER INFORMATION: Recombinant polynucleotide

<400> SEQUENCE: 100

| | | |
|---|---|---|
| cagcctgggg ggtccctgtg tctctcctgt gcagcctccg gatatatctt tagcgattag | 60 |
| gctatgggct gggtccgcca ggctccaggg aagggtctag agtgggtatc aagcattcat | 120 |
| accgcaaacg gtagcacata ctacgcagac tccgtgaagg gccggttcac catctcccgt | 180 |
| gacaattcca gaacacgct gtatctgcaa atgaacagcc tgcgtgccga ggacacctcg | 240 |
| gtatattatt gcgcgggtta tagtgagtgg taggacgaga tgcagtattg ggtcaggga | 300 |
| accctggtca ccgtctcgag cgcggccgca gaacaaaaac tcatctcaga agaggatct | 359 |

<210> SEQ ID NO 101
<211> LENGTH: 337
<212> TYPE: DNA
<213> ORGANISM: Artificial Sequence
<220> FEATURE:
<223> OTHER INFORMATION: Recombinant polynucleotide

<400> SEQUENCE: 101

| | | |
|---|---|---|
| tatcctgtgc agcctccgga tatatcttta gcgattaggc tatgggcagg gtccgccagg | 60 |
| ctccagggaa gggtctagag tgggtatcaa gcattcatac cgcaaacggt agcacatact | 120 |
| tcacaaaatc cgtgaagggc cggttcacca tctcccgtga caattccaag aacacgctgt | 180 |
| atctgcaaat gaacagcctg cgtgccgagg acaccgcggt atattattgc gcgggttata | 240 |
| gtgagtggta ggacgagatg cagtattggg gtcagggaac cctggtcacc gtctcgagcg | 300 |
| cggccgcaga acaaaaactc atttctttag aggatct | 337 |

<210> SEQ ID NO 102
<211> LENGTH: 407
<212> TYPE: DNA
<213> ORGANISM: Artificial Sequence
<220> FEATURE:
<223> OTHER INFORMATION: Recombinant polynucleotide

<400> SEQUENCE: 102

| | | |
|---|---|---|
| atggcccagg tgcagctgtt ggagtctggg ggaggcttgg tacagcctgg ggggtccctg | 60 |

```
cgtctctcct gtgcagcctc cggatttatc gttagcgctt aggctatgag ctgggtccgc      120
caggctccag ggaagggtct agagtgggta tcaggcattg gggcgggaaa cggtagcaca      180
tactacgcag actccgtgaa gggccggttc accatctccc gtgacaattc caagaacacg      240
ctgtatctgc aaatgaacag cctgcgtgcc gaggacaccg cggtatatta ttgcgcgagt      300
actaaggagc tgtttgagtc cacgaccgtc ggctcttggg gtcagggaac cctggtcacc      360
gtctcgggcg cggccgcaga acaaaaactc atctcagaag aggatct                   407

<210> SEQ ID NO 103
<211> LENGTH: 401
<212> TYPE: DNA
<213> ORGANISM: Artificial Sequence
<220> FEATURE:
<223> OTHER INFORMATION: Recombinant polynucleotide

<400> SEQUENCE: 103
atggcccagg tgcagctgtt ggagtctggg ggaggcttgg tacagcctgg ggggtccctg       60
cgtctctcct gtgcagcctc cggatttaag attatcgatt acgatatggg ctgggtccgc      120
caggctccag ggaagggtct agagtgggta tcaagcattt agaacagaag cggtagcaca      180
tactacgcag actccgtgaa gggccggttc accatctccc gtgacaattc caagaacacg      240
ctgtatctgc aaatgaacag cctgcgtgcc gaggacaccg cggcatatta ttgcgcgggt      300
tatgggaggt aggacgagac ggtcgactct tggggtcagg gaaccctggt caccgtctcg      360
agcgcggccg cagaacaaaa actcatctca gaagaggatc t                         401

<210> SEQ ID NO 104
<211> LENGTH: 422
<212> TYPE: DNA
<213> ORGANISM: Artificial Sequence
<220> FEATURE:
<223> OTHER INFORMATION: Recombinant polynucleotide

<400> SEQUENCE: 104
atggcccagg tgcagctgtt ggagtctggg ggaggcttgg tacagcctgg ggggtccctg       60
cgtctctcct gtgcagcctc cggagttaac cttagcgatg acactatggg ctgggtccgc      120
caggctccag ggaagggtct agagtgggta tcaggcattg ataacacaga cggtagcaca      180
tactacgcag actccgtgaa gggccggttc accatctccc gtgacaattc caagaacacg      240
ctgtatctgc aaatgaacag cctgcgtgcc gaggacaccg cggtatatta ttgcgcggga      300
gagggtctgc agttggtggc gctgcttggt gattcggcgg acgtggactt ttggggtcag      360
ggaaccctgg tcaccgtctc gagcgcggcc gcagaacaaa aactcatctc agaagaggat      420
ct                                                                   422

<210> SEQ ID NO 105
<211> LENGTH: 395
<212> TYPE: DNA
<213> ORGANISM: Artificial Sequence
<220> FEATURE:
<223> OTHER INFORMATION: Recombinant polynucleotide

<400> SEQUENCE: 105
atgcttccgg ctcgtatgtt gtgtggaatt gtgagcggat aacaatttca cacaggaaac       60
agctatgacc atgattacgc caagcttaac tctcagtata tgagctgggt ccgccaggct      120
ccagggaagg gtctagagtg ggtatcagcc attactaccc ctgacggtag cacatactac      180
```

```
gcagactccg tgaagggccg gttcaccatc tcccgtgaca attccaagaa cacgctgtat    240
ctgcaaatga acagcctgcg tgccgaggac accgcggtat attattgcgc gggtcaggat    300
ggtaatcagg aggacatccg cttttggggt cagggaaccc tggtcaccgt ctcgagcgcg    360
gccgcagaac aaaaactcat ctcagaagag gatct                              395
```

<210> SEQ ID NO 106
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 106

```
ggctcgtatg ttgtgtggaa ttgtgagcgg ataacaattt cacacaggaa acagctatga     60
ccatgattac gccaagctta actctcagta tatgagctgg gtccgccagg ctccagggaa    120
gggtctagag tgggtatcag ccattgctac ccctgacggt agcacatact acgcagactc    180
cgtgaagggc cggttcacca tctcccgtga caattccaag aacacgctgt atctgcaaat    240
gaacagcctg cgtgccgagg acaccgcggt atattattgc gcgggtcagg atggtaatca    300
ggaggacatc cgcttttggg gtcagggaac cctggtcacc gtctcgagcg cggccgcaga    360
acaaaaactc atctcagaag aggatct                                        387
```

<210> SEQ ID NO 107
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 107

```
ggctcgtatg ttgtgtggaa ttgtgagcgg ataacaattt cacacaggaa acagctatga     60
ccatgattac gccaagctta actctcagta tatgagctgg ggccgccagg ctccagggaa    120
gggtctagag tgggtatcag ccattgctac ccctgacggt agcacatact acgcagactc    180
cgtgaagggc cggttcacca tctcccgtga caattccaag aacacgctgt atctgcaaat    240
gaacagcctg cgtgccgagg acaccgcggt atattattgc gcgggtcagg atggtaatca    300
ggaggacatc cgcttttggg gtcagggaac cctggtcacc gtctcgagcg cggccgcaga    360
acaaaaactc atctcagaag aggatct                                        387
```

<210> SEQ ID NO 108
<211> LENGTH: 387
<212> TYPE: DNA
<213> ORGANISM: Artificial Sequence
<220> FEATURE:
<223> OTHER INFORMATION: Recombinant polynucleotide

<400> SEQUENCE: 108

```
ggctcgtatg ttgtgtggaa ttgtgagcgg ataacaattt cacacaggaa acagctatga     60
ccatgattac gccaagctta actctcagta tatgagctgg gtccgccagg ctccagggaa    120
gggtctagag tgggtatcag ccattactac ccctgacggt agcacataat acgcagactc    180
cgtgaagggc cggttcacca tctcccgtga caattccaag aacacgctgt atctgcaaat    240
gaacagcctg cgtgccgagg acgcgcggt atattattgc gcgggtcagg atggtaatca    300
ggaggacatc cgcttttggg gtcagggaac cctggtcacc gtctcgggcg cggccgcaga    360
acaaaaactc atctcagaag aggatct                                        387
```

<210> SEQ ID NO 109
<211> LENGTH: 382
<212> TYPE: DNA
<213> ORGANISM: Artificial Sequence
<220> FEATURE:
<223> OTHER INFORMATION: Recombinant polynucleotide

<400> SEQUENCE: 109

```
gtatggtgtg gggaattgtg agcggataac aatttcacac aggaaacaac tatgaccatg      60
attacgccaa gcttgactct caggatatga gctgggtccg ccaggctcca gggaagggtc     120
tagagtgggt atcagccatt actaccctg acggtagcac atactacgca gactccgtga     180
agggccggtt caccatctcc cgtgacaatt ccaagaacac gctgtatctg caaatgaaca     240
gcctgcgtgc cgaggacacc gcggtatatt attgcgcggg tcaggatggt aatcaggagg     300
acatccgctt ttggggtcag ggaaccctgg tcaccgtctc gagcgcggcc gcagaacaaa     360
aactcatctc agaagaggat ct                                              382
```

<210> SEQ ID NO 110
<211> LENGTH: 429
<212> TYPE: DNA
<213> ORGANISM: Artificial Sequence
<220> FEATURE:
<223> OTHER INFORMATION: Recombinant polynucleotide

<400> SEQUENCE: 110

```
atggcccagg tgcagctgtt ggagtctggg ggaggcttgg tacagcctgg ggggtccct      60 gcgtctctcc tgtgcagcct ccggagataa ccttacccat tagactatga cctgggtccg     120
ccaggctcca gggaagggtc tagagtgggt atcaagcatt tcgaccacaa gcggtagcac     180
atactacgca gactccgtga agggccggtt caccatctcc cgtgacaatt ccaagaacac     240
gctgtatctg caaatgaaca gcctgcgtgc cgaggacacc gcggtatatt attgcgcggg     300
tgggcagaat ccgggtcagg tgctttatgt ttctgctagt ccgcaggcgt tcgattttg      360 gggtcaggga accctggtca ccgtctcgag cgcggccgca gaacaaaaac tcatctcaga     420
agaggatct                                                             429
```

<210> SEQ ID NO 111
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 111

```
cgactgcaga tgaatatacc ttgctttgtt gtgattc                               37
```

<210> SEQ ID NO 112
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 112

```
cgtggtacct catgtacctg gaagcccttt ataggactc                             39
```

<210> SEQ ID NO 113
<211> LENGTH: 33
<212> TYPE: DNA

<213> ORGANISM: Artificial Sequence
<220> FEATURE:
<223> OTHER INFORMATION: Synthetic polynucleotide

<400> SEQUENCE: 113

```
catctgctag caatggcttc ctactttgcg ttg                                    33
```

<210> SEQ ID NO 114
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 114

```
ttcaatggta ccttattggg cagtttgtcc ctt                                    33
```

<210> SEQ ID NO 115
<211> LENGTH: 1569
<212> TYPE: DNA
<213> ORGANISM: Mokola virus

<400> SEQUENCE: 115

```
atgaatatac cttgctttgt tgtgattctt ggattcacaa ctacatattc tcttggggaa       60
tttcctttgt acacaattcc cgagaagata gagaaatgga ccccaataga catgatccat      120
ctaagctgcc ccaacaactt attatccgag gaggaaggtt gcaatacaga gtcgcccctc      180
acctacttcg agctcaagag tggttactta gctcatcaga agttccgggg gtttacctgt      240
acaggggtag tgaatgaggc ggagacatac acaaattttg tcgggtatgt cacccacaaac     300
ttcaaaagaa aacactttaa gcctacagtc tccgcctgtc gtgatgccta caactggaaa      360
gcgtccgggg atcccaggta tgaggagtca ctgcacactc cttaccctga cagcagctgg      420
ttgagaactg taactaccac caaagaatcc cttcttataa tatcgcctag catcgtggag      480
atggatgtat atgcaggac tctccattcc cccatgttcc cttcaggat gttctaag           540
ctctatccct ctgttccatc ctgcaaaacc aaccatgatt acacattatg gctgccagaa      600
gatcctagtt tgagtttaat ctgtgatatt ttcacttctg gcagcggaag gaaggccatg      660
aatgggtccc gcatctgcgg attcaaggat gaaagggat tttacagatc tttgaaaggc      720
gcttgtaagc tgacattgtg cggaaggcct gggatcagat tatttgacgg aacttgggtc      780
tcttttacaa ggccagaagt tcacgtgtgg tgcaccccta ccaattggt caatatacac      840
aatgatagaa tagatgagat cgagcacctg attgttgaag acattgtcaa agaaggggag      900
gagtgtttag acactctaga cagtattttt atgtctcaat caattagttt taggaggttg      960
agccactttc ggaaattggt tcccggatat gggaaagctt acaccatttt gaatggtagc     1020
ctgatggaag caaatgtcta ctataaaaga gttgacaggt gggcggacat tttaccctct     1080
aagggatgtc tgaaagtcgg gcaacaatgt atggaccctg tcaacggagt cctcttcaat     1140
gggattatca aggtccaga tggccagatc ttgatccctg aaatgcagtc agagcagctc     1200
aagcagcata tggacttatt aaaggcagca gtgttccctc tcagacatcc tttaatcagc     1260
caagacgcca tctttaagaa agacggggag gcagatgatt ttgtggacct ccatatgcca     1320
gatgtacaca atctgtatc agatgtcgac ttgggtttgc ctcactgggg gttttggatg     1380
ttgatcgggg caactgtagt ggcattttttg gtcttggtgt gtctgctccg tgtctgctgt     1440
aagagagtga ggaggagagg ttcacgacgt acaactcagg agatccccct caacgtttcc     1500
tctgtccccg tccctcgggc cacagtggtg tcatcatggg agtcctataa agggcttcca     1560
```

```
ggtacatga 1569

<210> SEQ ID NO 116
<211> LENGTH: 1578
<212> TYPE: DNA
<213> ORGANISM: West caucasian bat virus
<400> SEQUENCE: 116
atggcttcct actttgcgtt ggtcttgaac gggatctcta tggttttcag tcaaggtctt 60
ttccccttt acactatccc tgaccatctg ggaccatgga cccccataga tctaagtcac 120
cttcactgcc cgaacaatct ttatactgat gcctcttatt gtacaactga acaaagcata 180
acctacacag agttgaaggt cggatcatct gtgtcacaaa aaatccccgg atttacatgt 240
acgggggtaa gaactgaatc tgtaacatat accaactttg ttggctatgt gactaccacg 300
ttcaagaaaa aacactttcc tcctaaatcc agggactgta gagaggcgta tgagaggaag 360
aaagcaggag atcctagata tgaagagtct ttagcccacc catatcctga caacagttgg 420
ctgagaacag tgactacaac aaaggattcc tgggtgatca tcgagcccag tgtagtggag 480
ttagatatat acacaagtgc cttgtattca cctcttttca aggatggaac atgttcaaaa 540
tctagaacat attcccccta ctgtccaacc aatcatgact tcaccatttg gatgccagag 600
agtgaaaaca taagatctgc ctgtaatctg ttttccacaa gtagagggaa actagtcagg 660
aaccgcacat ccacctgcgg gattatcgat gagagagggc tgttcagatc agttaaagga 720
gcatgcaaaa tatcaatatg cggtaggcag ggaatccgtt tagtggatgg aacttggatg 780
tcttttagat actcagagta cttacctgtg tgttctccat cacagctgat caacacgcac 840
gacatcaagg tcgatgagct ggagaatgct atagttttag acttgattag gaggagagaa 900
gaatgtcttg acaccctaga aacaattttg atgtcaggat ctgtgagtca caggaggctg 960
agtcatttca gaaagctggt tccaggatct gggaaggctt actcttatat aaacggcacc 1020
ttaatggaat cagatgctca ctacatcaag gtagagaatt ggtcagaggt catcccacac 1080
aaaggatgtc tcatggtcgg gggcaaatgc tatgagccag tcaatgatgt gtatttcaac 1140
gggatcattc gggattcaaa taatcagatc ttgatacctg agatgcagtc cagtcttctc 1200
agagaacatg ttgacctgtt gaaggctaat atagttccgt tcaggcatcc aatgttactt 1260
aggtccttca catctgacac tgaagaagat atcgtcgagt ttgtcaaccc tcatctccaa 1320
gatacccaga agttggtgtc agatatggat ctcgggttat cagactggaa gagatatcta 1380
ctaattggat ctttggccgt aggaggagtg gtagcaatct tattcatcgg aacatgttgt 1440
ctgagatgta gagcagggag aaacagaaga acaatccgat ccaatcatag gtcattgtcc 1500
catgacgtgg tgttccataa agataaggat aaagtgatta cttcttggga atcttacaag 1560
ggacaaactg cccaataa 1578

<210> SEQ ID NO 117
<211> LENGTH: 53
<212> TYPE: DNA
<213> ORGANISM: Artificial Sequence
<220> FEATURE:
<223> OTHER INFORMATION: Synthetic polynucleotide
<400> SEQUENCE: 117
ttttttgat tgtggggagg aaagcgacgt caaaccatgg cagctctttt ttt 53

<210> SEQ ID NO 118
```

<211> LENGTH: 1569
<212> TYPE: DNA
<213> ORGANISM: Lagos bat virus

<400> SEQUENCE: 118

```
atgagtcaac taaatttgat accctttttc tgtgtaatta tagtcttgtc tgtagaggac      60
tttcctctat atacaattcc tgaaaagata ggtccttgga ctccgatcga cctgatccat     120
ctgagctgtc ctaataattt gcagtcagag gatgaaggat gtggtacctc atcagtcttc     180
agttatgtag agctcaagac aggttatctc actcatcaga aagtgtctgg gttcacctgt     240
acaggagtgg ttaatgaggc tgtcacatac actaactttg tcggatatgt gacaaccacc     300
tttaagcgga acatttcaa gccgacggca ttggcttgca gagatgctta tcattggaag     360
atttctgggg atccaaggta tgaggagtct ctccacacac catatcctga aacagctgg      420
ttgaggacag ttaccacaac caagaatct cttgtgataa tctctccaag cattgtggag     480
atggatgtat atagtagaac acttcattct cccatgtttc ccaccgggac ctgttctagg     540
ttctatccgt catcccttc ttgtgccaca aatcatgatt acactttatg cttccagat      600
gaccctaatc tgagtttggc atgtgatatc tttgtgacca gcacagggaa aaagtcaatg     660
aatggctcta atgtgtgg atttacagac gagagagggt attaccggac aataaaagga      720
gcttgtaaac tgacattatg tgggaaacca ggtttgaggt tatttgatgg cacatggata     780
tccttccccc gcccggaagt cactacccgg tgccttccta atcagttagt caatattcac     840
aacaatagga tagatgaagt tgagcatctg attgtagaag atctcattcg aaaaagagaa     900
gagtgtttgg acactttaga gacagtttta atgtccaaat caatcagttt tagacgacta     960
agtcacttca gaaaattagt gccaggatat gggaaggctt acactatttt aaatgggagc    1020
ttaatggaaa ctaacgttca ttatttaaag gttgacaatt ggagtgaaat actgccttcc    1080
aagggatgtt taaaaataaa caatcagtgt gttgctcatt ataagggggt cttctttaac    1140
gggatcatca agggaccaga tggtcatatt ttaatccccg agatgcagtc aagtttgttg    1200
aaacagcaca tggacctctt gaaggcagcg ttttttccct tgaaacatcc tctgattgaa    1260
ccgggctctt tgttcaataa ggatggtgat gccgatgaat tgttgatgt ccacatgcct    1320
gatgtacata agttggtatc agatgtcgac ttggggctac ccgattggag cctttatgcg    1380
ttgataggg caactattat agctttcttt tactgatat gtcttattcg tatctgctgc    1440
aagaaggggg gtcggagaaa ctctcccaca aatagacctg atcttcctat agggttgtct    1500
actacacctc aacccaagtc taaagtgata tcatcatggg aatcttataa gggtaccctc    1560
aatgtctga                                                            1569
```

<210> SEQ ID NO 119
<211> LENGTH: 1602
<212> TYPE: DNA
<213> ORGANISM: Duvenhage virus

<400> SEQUENCE: 119

```
atgccactca atgcagtcat atttactctt ctcctcagat gttccatctg cctgggaaag      60
tttccatttt atcgatccc tgacaaattg gggccatgga gccctataga catacatcat     120
ctcagttgcc caaataactt ggttgtggaa gacgaaggat gtacaactct aaccccttt      180
tcatacatgg agttaaaggt aggttacatt acatcaataa aggtgtccgg ttttaccctgc     240
actggggtag tgactgaagc tgagacttat accaatttcg ttgggtatgt gacgacaaca     300
tttagaagaa gacatttccg tccatcagtc aactcttgta gagatgcata caattggaag     360
```

```
atcgcaggag accctaggta tgaagaatca ctacacaacc cttatccaga ctctcactgg    420
ctcagaactg tcaagactac aaaagaatct cttttgataa tctccccag cgtggctgac    480 atggatgcgt atgacaagaa gctttactcc aagattgttt ccaacggaag gtgttcggaa    540
atatctcctg ggtcccctt ctgtcccacc aatcatgaat acactatctg gatgcccgag    600
agctcaaacc ccggaatatc ctgtgacata ttcacaagaa gcatggggaa gaaagccacc    660
aaagatggac agttatgtgg gtttgtagat gagagaggac tgtacaaatc tctgaaggga    720
gcttgtagat taagactctg tgggatcagc ggactgagac tgatggacgg gtcatgggtt    780
tcactcccac aggttaacaa ctcagaatgg tgctccccag accaacttgt taacattcac    840
gacttccatt cagatgagat agagcatctc gtcgcagatg agttggtgaa aaagagagag    900
gattgtctag acgcccttga aactatcctc ttcaccaaat ctataagttt ccggcgttta    960
agccatcttc ggaagctagt tccaggcttt ggtaaggcat atactatcat aaataggacc   1020
cttatggaag cagaggctca ttacaagtca gtgcgggagt ggaaggaaat tattccatcc   1080 aagggggtgtc tgaaggcagg agggaggtgc tatcctcatc acaatggaat tttcttcaac   1140
gggatcattc tgggtccggg aggggagatc ttgatccctg agatgcagtc tgccttgctc   1200
caacagcaca ttgagctgtt agagtcctct gtagttcccc tcaaacaccc cctggcagac   1260
ccttcgactg tcttcaagaa cgatgatgaa gcggagagtt tcgtagatgt tcaccttcct   1320
gatacaaacc aaaaaatatc tggaattgac ttagggttgc cagagtggaa acgttacttc   1380
ctaataggag tctcagcagt tgctttgttg gctttatcta taattatcgc tgtctgttgc   1440
aaaaggttca ggaaaaggaa gaaatccaaa cccggtccag tagaattgac tagaaaagtg   1500
tctgtcatat ccaaaggaaa tggaccggtc ccttcctggg aatcttataa agaaggaacc   1560
acaggagatg ttcgtaatac gactccatca acaagggagt ga                      1602
```